United States Patent [19]
Bolton et al.

[11] Patent Number: 5,208,224
[45] Date of Patent: May 4, 1993

[54] PHOSPHORUS CONTAINING COMPOUNDS AS ANTIHYPERCHOLESTEROLEMIC AND ANTIATHEROSCLEROTIC AGENTS

[75] Inventors: Gary L. Bolton; Janak K. Padia, both of Ann Arbor; Bharat K. Trivedi, Farmington Hills, all of Mich.

[73] Assignee: Warner-Lambert Company, Morris Plains, N.J.

[21] Appl. No.: 668,534

[22] Filed: Mar. 13, 1991

[51] Int. Cl.$^5$ .............. A61K 31/66; C07F 9/32; C07F 9/40; C07F 9/46
[52] U.S. Cl. .................. 514/110; 514/114; 514/115; 514/118; 514/119; 514/120; 558/81; 558/154; 558/170; 558/171; 558/172; 558/179; 558/181; 560/38; 560/105; 560/130; 562/10; 562/11; 562/15; 562/16; 562/24; 564/12; 564/14; 568/15
[58] Field of Search .............. 558/81, 154, 170, 171, 558/172, 179, 181; 560/38, 105, 130; 562/10, 11, 15, 16, 24; 564/12, 14; 568/15; 514/110, 114, 115, 118, 119, 120

[56] References Cited

U.S. PATENT DOCUMENTS

| | | | |
|---|---|---|---|
| 2,754,320 | 7/1956 | Johnston | 558/170 X |
| 2,963,458 | 12/1960 | Swern | 558/179 X |
| 3,384,683 | 5/1968 | Schwarze | 260/938 |
| 3,385,689 | 5/1968 | Richter | 71/87 |
| 3,449,109 | 6/1969 | Richter | 71/87 |
| 3,980,614 | 9/1976 | Noetzel et al. | 562/15 X |
| 4,105,689 | 8/1978 | Auer et al. | 562/15 |
| 4,536,346 | 8/1985 | Shepherd et al. | 260/465 |

FOREIGN PATENT DOCUMENTS 780800  3/1968  Canada .................. 71/8.9

OTHER PUBLICATIONS

Srivastava et al., Chemical Abstracts, vol. 68 (1968) 12627b.
Murayama et al, Chemical Abstracts, vol. 85(1976) 144593y.
Morita et al, Chemical Abstracts, vol. 89 (1978) 146990g.
Endo et al, Chemical Abstracts, vol. 89 (1978) 44990q.
Tsivunin et al, Chemical Abstracts, vol. 74 (1971) 53927s.
Pudovik et al, Chemical Abstracts, vol. 72 (1970) 12830v.
Noetzel et al, Chemical Abstracts, vol. 85 (1976) 47586r.
Zabusova et al, Chemical Abstracts, vol. 66 (1967) 10998h.
Pudovik et al, Chemical Abstracts, vol. 80 (1974) 83134x.
Khairullin et al, Chemical Abstracts, vol. 69 (1968) 59335r.
Pudovik et al, Chemical Abstracts, vol. 70 (1969) 115241s.
Pudovik et al, Chemical Abstracts, vol. 71 (1969) 3478p.
Lomakina et al, Chemical Abstracts, vol. 63 (1965) 15477c.
Kijima et al, Chemical Abstracts, vol. 88 (1978) 136815u.
Mel'nikov et al, Chemical Abstracts, vol. 57 (1961) 117072c.
Garibina et al., Chemical Abstracts, vol. 105 (1986) 133978.

*Primary Examiner*—Richard L. Raymond
*Attorney, Agent, or Firm*—Francis J. Tinney

[57] ABSTRACT

Novel phosphorus containing compounds are described, as well as methods for the preparation and pharmaceutical composition of same, which are useful in preventing the intestinal absorption of cholesterol and thus are useful in the treatment of hypercholesterolemia and atherosclerosis.

6 Claims, No Drawings

PHOSPHORUS CONTAINING COMPOUNDS AS ANTIHYPERCHOLESTEROLEMIC AND ANTIATHEROSCLEROTIC AGENTS

BACKGROUND OF THE INVENTION

The present invention relates to novel phosphorus containing compounds useful as pharmaceutical agents, to methods for their production, to pharmaceutical compositions which include these compounds, and a pharmaceutically acceptable carrier, and to pharmaceutical methods of treatment. More particularly, the novel compounds of the present invention prevent the intestinal absorption of cholesterol in mammals by inhibiting the enzyme acyl-coenzyme A (Acyl-CoA):cholesterol acyltransferase (ACAT).

The atheromatous plaque, which is the characteristic lesion of atherosclerosis, results from deposition of plasma lipids, mainly cholesteryl esters, in the intima of the arterial wall. Progressive enlargement of the plaque leads to arterial constriction and ultimately coronary heart disease. A number of clinical trials have shown a causal relationship between hypercholesterolemia and coronary heart disease.

Agents that control dietary cholesterol absorption moderate serum cholesterol levels. Dietary cholesterol is absorbed from the intestinal lumen as free cholesterol which must be esterified with fatty acids. This reaction is catalyzed by the enzyme acyl-CoA:cholesterol acyltransferase (ACAT). The resulting cholesteryl esters are packaged into the chylomicrons which are secreted into the lymph. Inhibitors of ACAT not only prevent absorption of dietary cholesterol but also prevent the reabsorption of cholesterol which has been released into the intestine through endogenous regulatory mechanisms, thus lowering serum cholesterol levels and ultimately counteracting the formatting or development of atherosclerosis.

Compounds of the formula

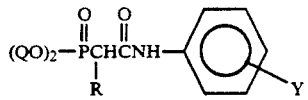

wherein R is selected from the group consisting of hydrogen, $C_1-C_4$ alkyl, phenyl, and phenyl substituted with X; X represents one or more substituents independently selected from the group consisting of hydrogen, $C_1-C_4$ alkyl, hydroxy, $C_1-C_4$ alkoxy, halo, and nitro; Y represents one or more substituents independently selected from the group consisting of hydrogen, $C_1-C_4$ alkyl, hydroxy, $C_1-C_4$ alkoxy, halo, trifluoromethyl, nitro, amino, acetamido, acetyl, formyl, cyano, carboxy, $C_1-C_4$ carboalkoxy, carboxamido, sulfonamido, —$CO_2CH_2CO_2C_2H_5$, —$CO_2CH_2CO_2CH_3$, and —$CO_2CH_2CO_2H$; and Q is selected from the group consisting of $C_1-C_4$ alkyl and phenyl are disclosed as intermediates to prepare a series of substituted aralkanamidobenzoic acids in U.S. Pat. No. 4,536,346.

A method of controlling undesirable plant growth with a compound of the general formula

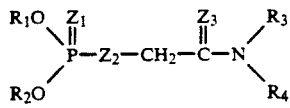

wherein $Z_1$, $Z_2$, and $Z_3$ are independently selected from the group consisting of sulfur and oxygen; $R_1$ is aryl; $R_2$ is selected from the group consisting of alkyl, aralkyl and aryl; $R_3$ and $R_4$ are independently selected from the group consisting of alkyl, hydroxyalkyl, unsubstituted aryl, substituted aryl, alkenyl, aralkyl, and hydrogen; provided a maximum of one of $R_3$ and $R_4$ is hydrogen. It is preferred that $R_1$ be selected from the group consisting of unsubstituted aryl containing six to ten carbon atoms and substituted aryl wherein the substituents are selected from the group consisting of alkyl containing one to ten carbon atoms, halogen and mixtures thereof; $R_2$ be independently selected from the group consisting of alkyl containing one to ten carbon atoms, aralkyl containing seven to twenty carbon atoms, and aryl containing six to twenty carbon atoms; $R_3$ and $R_4$ be independently selected from the group consisting of alkyl containing one to ten carbon atoms, hydroxyalkyl containing one to ten carbon atoms, unsubstituted aryl containing six to ten carbon atoms, substituted aryl wherein the substituents are selected from the group consisting of alkyl containing one to ten carbon atoms, halogen and mixtures thereof, alkenyl containing two to ten carbon atoms, aralkyl containing seven to twenty carbon atoms and hydrogen, provided a maximum of one of $R_3$ and $R_4$ is hydrogen is disclosed in U.S. Pat. No. 3,385,689.

A process for controlling undesirable plant life with the use of chemical compounds of the general formula

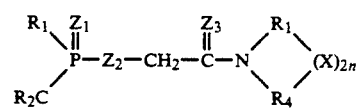

wherein $Z_1$, $Z_2$, and $Z_3$ are independently selected from the group consisting of sulfur and oxygen; $R_1$ is aryl; $R_2$ is selected from the group consisting of alkyl, aralkyl and aryl; $R_3$ and $R_4$ are independently selected from the group consisting of alkyl, alkylene, acyl, aryl, aralkyl, hydroxyalkyl, alkenyl, cycloalkyl, and hydrogen provided that a maximum of one of $R_3$ and $R_4$ is hydrogen; n is an integer of from 0 to 1; and X is selected from the group consisting of oxygen, sulfur, >NY and >CHY wherein Y is selected from the group consisting of lower alkyl and hydrogen, provided that when n is 0, $R_3$ and $R_4$ are selected from the group consisting of alkyl, acyl, aryl, aralkyl, hydroxyalkyl, alkenyl, cycloalkyl, and hydrogen provided that a maximum of one of $R_3$ and $R_4$ is hydrogen and when n is 1, $R_3$ and $R_4$ are alkylene is disclosed in U.S. Pat. No. 3,449,109.

A series of compounds of the formula

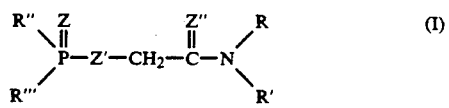

wherein R is independently selected from the group consisting of alkyl, alkoxy, hydroxyalkyl, alkenyl, aryl, aralkyl, and cycloalkyl groups and hydrogen; R' is independently selected from the group consisting of alkyl, hydroxyalkyl, aryl, alkenyl, aralkyl, and cycloalkyl groups and hydrogen, provided that a maximum of one of R and R, is hydrogen; Z, Z', and Z" are independently selected from the group consisting of oxygen and sulfur; and R" and R''' are independently selected from the group consisting of alkyl, cycloalkyl, alkoxy, cycloalkoxy, alkylthio, aryl, aryloxy, arylthio, aralkyl, aralkoxy, and aralkylthio groups, provided that when one or both of R and R' are selected from the group consisting of hydroxyalkyl, alkenyl, aryl, aralkyl, and cycloalkyl groups and hydrogen, or R is alkyl, R'' is selected from the group consisting of alkoxy, aralkoxy, and aryloxy, and R''' is aryloxy useful for the control of undesirable plant life is disclosed in Canadian Patent 780,800.

A series of compounds of the formula

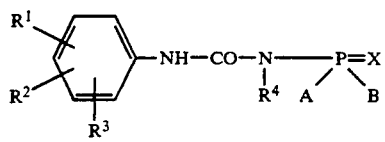

in which each of $R_1$, $R_2$, and $R_3$ are hydrogen, halogen, preferably chlorine, alkyl, preferably of one to four carbon atoms, or nitro, $R_4$ is lower alkyl, preferably with one to four carbon atoms, X is oxygen or sulfur and each of A and B is alkyl amino such as mono- and dialkyl amino or alkoxy, preferably those where the alkyl is of one to four carbon atoms useful as plant growth regulating compounds is disclosed in U.S. Pat. No. 3,384,683.

However, the compounds described in the aforementioned references do not disclose or suggest the combination of structural variations nor the use in preventing the intestinal absorption of cholesterol of the compounds of the present invention described hereinafter.

SUMMARY OF THE INVENTION

Accordingly, the present invention is a novel class of compounds of Formula I

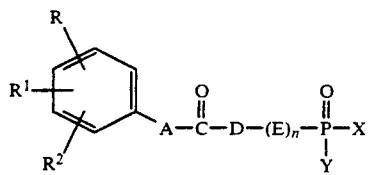

wherein

R, $R^1$, and $R^2$ are each independently hydrogen, alkyl of from one to six carbon atoms, alkoxy of from one to six carbon atoms, halogen or trifluoromethyl;

A is O or NH;

D is $CH_2$ or N—$R^4$ wherein $R^4$ is hydrogen, alkyl of from one to six carbon atoms, or —$CH_2$-aryl;

E is O, $CH_2$, or N—$R_4$ wherein $R^4$ is as defined above;

n is zero or one;

X and Y are each independently alkyl of from one to twenty carbon atoms, aryl,

—$OR^5$ wherein $R^5$ is hydrogen, alkyl of from one to twenty carbon atoms,

—$(CH_2)$m-aryl wherein m is zero or an integer of 1, 2, or 3 or

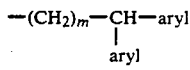

wherein m is as defined above

$R^6$ wherein $R^6$ and $R^7$ are each independently hydrogen, alkyl of from one to twenty carbon atoms, —$(CH_2)_o$-aryl wherein O is an integer of 1, 2, or 3 or

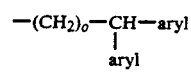

wherein O is as defined above or

X and Y are taken together with the phosphorus atom to which they are attached to form a ring denoted by

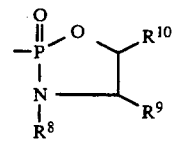

wherein $R^8$ is hydrogen, alkyl of from one to twenty carbon atoms, or

—$CH_2$-aryl and $R^9$ and $R^{10}$ are each independently hydrogen, alkyl of from one to twenty carbon atoms, or aryl; provided when A is NH, D is $CH_2$, n is zero, and R, $R^1$, and $R^2$ are as defined above both X and Y are not $OR^5$ wherein $R^5$ is alkyl of from one to four carbon atoms or phenyl; further provided when A is NH, D is $CH_2$, E is O, n is one and R, $R^1$, and $R^2$ are as defined above one of X or Y is

wherein $R^6$ and $R^7$ are as defined above or X and Y are taken together with the phosphorus atom to which they are attached to form a ring denoted by

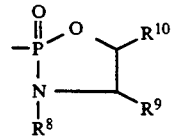

wherein $R^8$, $R^9$, and $R^{10}$ are as defined above; and finally provided when X and Y are both —$OR^5$ wherein $R^5$ is alkyl of from one to twenty carbon atoms or

wherein $R^6$ and $R^7$ are each independently alkyl of from one to twenty carbon atoms, A is NH, n is zero and R, $R^1$ and $R^2$ are as defined above D is $N-R^4$ wherein $R^4$ is hydrogen, or $-CH_2$-aryl; or a pharmaceutically acceptable base addition salt thereof.

Additionally, the present invention is directed to a novel method of treating hypercholesterolemia or atherosclerosis comprising administering to a mammal in need of such treatment an acyl-coenzyme A:cholesterol acyltransferase-inhibitory effective amount of a compound of Formula I in unit dosage form.

Also, the present invention is directed to a pharmaceutical composition for treating hypercholesterolemia or atherosclerosis comprising an acyl-coenzyme A:-cholesterol acyltransferase-inhibitory effective amount of a compound of Formula I in combination with a pharmaceutically acceptable carrier.

Finally, the present invention is directed to methods for production of a compound of Formula I.

DETAILED DESCRIPTION OF THE INVENTION

In the compounds of Formula I, the term "alkyl" means a straight or branched hydrocarbon radical having from one to twenty carbon atoms and includes, for example, methyl, ethyl, n-propyl, isopropyl, n-butyl, isobutyl, tertiary-butyl, n-pentyl, n-hexyl, n-heptyl, n-octyl, n-nonyl, n-decyl, undecyl, dodecyl, tridecyl, tetradecyl, pentadecyl, hexadecyl, heptadecyl, octadecyl, nonadecyl, eicodecyl, and the like.

"Alkoxy" is O-alkyl in which alkyl is as defined above.

"Halogen" is fluorine, chlorine, bromine, or iodine.

The term "aryl" means an aromatic radical which is a phenyl group or phenyl group substituted by one to three substituents selected from alkyl as defined above, alkoxy as defined above, halogen as defined above, or trifluoromethyl.

Certain of the compounds of Formula I are capable of further forming pharmaceutically acceptable base addition salts. Both of these forms are within the scope of the present invention. Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge, S. M., et al., "Pharmaceutical Salts," *Journal of Pharmaceutical Science*, 66, pp. 1–19 (1977)).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

A preferred compound of Formula I is one wherein X and Y are each independently aryl, $-OR^5$ wherein $R^5$ is hydrogen, alkyl of from one to twenty carbon atoms, $-(CH_2)_m$-aryl wherein m is zero or an integer of 1, 2, or 3, or

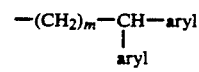

wherein m is as defined above,

wherein $R^6$ and $R^7$ are each independently
hydrogen,
alkyl of from one to fifteen carbon atoms,
$-(CH_2)_o$-aryl wherein O is an integer of 1 or 2,

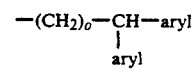

wherein O is zero or an integer of 1 or
X and Y are taken together with the phosphorus atom to which they are attached to form a ring denoted by

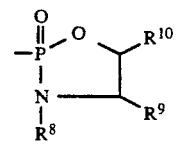

wherein
$R^8$ is alkyl of from one to six carbon atoms or
$-CH_2$-aryl and
$R^9$ and $R^{10}$ are each independently hydrogen,
alkyl of from one to fifteen carbon atoms or
aryl; provided when A is NH, D is $CH_2$, n is zero, and R, $R^1$, and $R^2$ are as defined above both X and Y are not $OR^5$ wherein $R^5$ is alkyl of from one to four carbon atoms or phenyl; further provided when A is NH, D is $CH_2$, E is O, n is one and R, $R^1$, and $R^2$ are as defined above one of X or Y is

wherein $R^6$ and $R^7$ are as defined above or X and Y are taken together with the phosphorus atom to which they are attached to form a ring denoted by

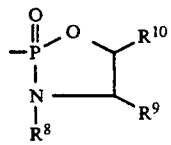

wherein $R^8$, $R^9$, and $R^{10}$ are as defined above; and finally provided when X and Y are both —$OR^5$ wherein $R^5$ is alkyl of from one to twenty carbon atoms or

wherein $R^6$ and $R^7$ are each independently alkyl of from one to twenty carbon atoms, A is NH, n is zero and R, $R^1$ and $R^2$ are as defined above D is N—$R^4$ wherein $R^4$ is hydrogen, or —$CH_2$-aryl.

Another preferred embodiment is a compound of Formula I wherein

X and Y are each independently aryl,
—$OR^5$ wherein $R^5$ is hydrogen alkyl of from one to fifteen carbon atoms, —$(CH_2)_m$-aryl wherein m is zero or an integer of 1 or,

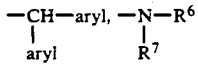

wherein $R^6$ and $R^7$ are each independently
hydrogen,
alkyl of from one to fifteen carbon atoms,
—$(CH_2)_o$-aryl wherein O is an integer of 1 or 2,

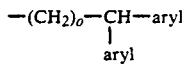

wherein O is zero or an integer of 1 or
X and Y are taken together with the phosphorus atom to which they are attached to form a ring denoted by

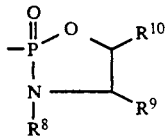

wherein
$R^8$ is alkyl of from one to six carbon atoms or —$CH_2$-aryl and
$R^9$ and $R^{10}$ are each independently hydrogen, alkyl of from one to fifteen carbon atoms or aryl; provided when A is NH,
D is $CH_2$, n is zero, and R, $R^1$, and $R^2$ are as defined above both X and Y are not —$OR^5$ wherein $R^5$ is alkyl of from one to four carbon atoms or phenyl; further provided when A is NH, D is $CH_2$, E is O, n is one and R, $R^1$, and $R^2$ are as defined above one of X or Y is

wherein $R^6$ and $R^7$ are as defined above or X and Y are taken together with the phosphorus atom to which they are attached to form a ring denoted by

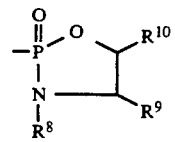

wherein $R^8$, $R^9$, and $R^{10}$ are as defined above; and finally provided when X and Y are both —$OR^5$ wherein $R^5$ is alkyl of from one to twenty carbon atoms or

wherein $R^6$ and $R^7$ are each independently alkyl of from one to twenty carbon atoms, A is NH, n is zero and R, $R^1$ and $R^2$ are as defined above D is N—$R^4$ wherein $R^4$ is hydrogen, or —$CH_2$-aryl.

Particularly valuable are:

(±)-[2-[[2,6-Bis(1-methylethyl)phenyl]amino]-2-oxoethyl]phenylphosphinic acid, ethyl ester;

N-[2,6-Bis(1-methylethyl)phenyl]-2-(diphenylphosphinyl)acetamide;

(±)-[2-Oxo-2-[2,4,6-trimethoxyphenyl)amino]-ethyl]-phenylphosphinic acid, ethyl ester;

(±)-[2-[(2,4-Difluorophenyl)amino]-2-oxoethyl]phenylphosphinic acid, ethyl ester;

(±)-[2-[[2,6-Bis(1-methylethyl)phenyl]amino]-2-oxoethyl]phosphonic acid, ethyl ester;

(±)-[2-[[2,6-Bis(1-methylethyl)phenyl]amino]-2-oxoethyl]phenylphosphinic acid;

(±)-[2-[[2,6-Bis(1 methylethyl)phenyl]amino]-2-oxoethyl]phosphonic acid, ethyl nonyl ester;

(±)-[2-[[2,6-Bis(1-methylethyl)phenyl]amino]-2-oxoethyl]-N-(diphenylmethyl)phosphonamidic acid, ethyl ester;

(±)-[2-[[2,6-Bis(1-methylethyl)phenyl]amino]-2-oxoethyl]-N,N-bis(phenylmethyl)phosphonamidic acid, ethyl ester;

(±)-[2-[[2,6-Bis(1-methylethyl)phenyl]amino]-2-oxoethyl]phenylphosphinic acid, 1-methyltridecyl ester;

(±)-[2-[[2,6-Bis(1-methylethyl)phenyl]amino]-2-oxoethyl]phenylphosphinic acid, 1-methylheptyl ester;

(±)-[2-[[2,6-Bis(1-methylethyl)phenyl]amino]-2-oxoethyl]phenylphosphinic acid, dodecyl ester;

(±)-[[[[[2,6-Bis(1-methylethyl)phenyl]amino]-carbonyl]amino]methyl]phosphonic acid, ethyl nonyl ester;

(±)-[[[[[2,6-Bis(1-methylethyl)phenyl]amino]-carbonyl]amino]methyl]phosphonic acid, ethyl diphenylmethyl ester;

(±)-[2-[[2,6-Bis(1-methylethyl)phenyl]amino]-2-oxoethyl]-N-(2,2-diphenylethyl)phosphonamidic acid, ethyl ester;

N-[[[2,6-Bis(1-methylethyl)phenyl]amino]-carbonyl]-phosphoramidic acid, diethyl ester;

(Diphenoxyphosphinyl)carbamic acid, 2,6-bis-(1-methylethyl)phenyl ester;

N-[[[2,6-Bis(1 methylethyl)phenyl]amino]-carbonyl]-phosphoramidic acid, diphenyl ester;

(±)-[[[2,6-Bis(1-methylethyl)phenyl]amino]carbonyl]-phosphoramidic acid, 4-(hexyloxy)phenyl phenyl ester;

(±) [[[2,6 Bis(1-methylethyl)phenyl]amino]carbonyl]-phosphoramidic acid, nonyl phenyl ester;

(±)-[[[2,6-Bis(1-methylethyl)phenyl]amino]carbonyl](-phenylmethyl)phosphoramidic acid, nonyl phenyl ester;

(±)-[[[2,6-Bis(1-methylethyl)phenyl]amino]carbonyl]-phosphoramidic acid, 2,6-bis(1-methylethyl)phenyl nonyl ester;

(±)-[[[[2,6 Bis(1-methylethyl)phenyl]amino]carbonyl]-methyl]phosphoramidic acid, 2,6-bis(1-methylethyl)-phenyl nonyl ester;

N-[[[2,6-Bis(1-methylethyl)phenyl]amino]carbonyl]-phosphoramidic acid, bis(phenylmethyl)ester;

(4S-cis)-N-[2,6-Bis(1-methylethyl)phenyl]-N'-(3,4-dimethyl-5-phenyl-1,3,2-oxazaphosphonolidin-2-yl)urea, P-oxide;

(±)-N-[[[2,6-Bis(1 methylethyl)phenyl]amino]carbonyl]-P-decylphosphonamidic acid, ethyl ester;

(±)-[[[(2,4,6-Trimethoxyphenyl)amino]carbonyl]amino]phosphoramidic acid, 1-methyltridecyl phenyl ester;

(±)-[[[2,6-Bis(1-methylethyl)phenyl]amino]carbonyl]-phosphoramidic acid, 1-methyltridecyl phenyl ester;

[[[[[2,6-Bis(1-methylethyl)phenyl]amino]carbonyl]amino]methyl]phosphonic acid, diethyl ester;

(±)-N-[2,6-Bis(1-methylethyl)phenyl]-2-[[5-decyl-3-(phenylmethyl)-1,3,2-oxazaphosphonolidin-2-yl]oxy]acetamide, P-oxide;

(±)-N-[2-[[2,6-Bis(1-methylethyl)phenyl]amino]-2-oxoethyl]-P-phenyl-N-(phenylmethyl)phosphonamidic acid, nonyl ester;

(±)-[2-[[2,6-Bis(1-methylethyl)phenyl]amino]-2-oxoethyl](phenylmethyl)phosphoramidic acid, ethyl nonyl ester;

(±)-N-[2-[2,6-Bis(1-methylethyl)phenyl]amino]-2-oxoethyl]phosphoramidic acid, nonyl phenyl ester;

(±)-[[[2,6-Bis(1-methylethyl)phenyl]amino]-2-oxoethyl](phenylmethyl)phosphoramidic acid, nonyl phenyl ester;

(±)-[2-[[2,6-Bis(1-methylethyl)phenyl]amino]-2-oxoethyl](phenylmethyl)phosphoramidic acid, 1-methyltridecylphenyl ester;

[2-[[2,6-Bis(1-methylethyl)phenyl]amino]-2-oxoethyl]-phosphonic acid, bis(phenylmethyl) ester;

(±)-P-[2-[[2,6-Bis(1-methylethyl)phenyl]amino]-2-oxoethyl]-N,N-dioctyl phosphonamidic acid, ethyl ester; and (±)-P-[2-[2,6-Bis(1-methylethyl)phenyl]amino]-2-oxoethyl]-N-methyl-N-(2-phenylethyl)phosphonamidic acid, ethyl ester; or a pharmaceutically acceptable base addition salt thereof.

The compounds of the present invention are potent inhibitors of the enzyme acyl-CoA:cholesteryl acyltransferase (ACAT), and are thus effective in inhibiting the esterification and transport of cholesterol across the intestinal cell wall. Thus, the compounds of the present invention are useful in pharmaceutical formulations for the inhibition of intestinal absorption of dietary cholesterol, the reabsorption of cholesterol released into the intestine by normal body action, or the modulation of cholesterol.

The ability of representative compounds of the present invention to inhibit ACAT was measured using an in vitro test more fully described in Field, F. J. and Salome, R. G., *Biochemica et Biophysica Acta*, Volume 712, pp. 557-570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes. The data in Table I is expressed as $IC_{50}$ values, i.e., the concentration of test compound required to inhibit cholesteryl oleate formation to 50% of control. The data in the table shows the ability of representative compounds of the present invention to potently inhibit ACAT.

TABLE 1

Biological Activity of Compounds of Formula I

| Example Number | Compound | $IC_{50}$ ($\mu$moles) |
|---|---|---|
| 1 | (±)-[2-[[2,6-Bis(1-methylethyl)phenyl]amino]-2-oxoethyl]-phenylphosphinic acid, ethyl ester | 0.65 |
| 2 | N-[2,6-Bis(1-methylethyl)phenyl]-2-(diphenylphosphinyl)-acetamide | 2.3 |
| 7 | (±)-[2-[[2,6-Bis(1-methylethyl)phenyl]amino]-2-oxoethyl]-phosphonic acid, ethyl nonyl ester | 0.090 |
| 9 | (±)-[2-[[2,6-Bis(1-methylethyl)phenyl]amino]-2-oxoethyl]- N,N-bis(phenylmethyl)phosphonamidic acid, ethyl ester | 0.048 |
| 10 | (±)-[2-[[2,6-Bis(1-methylethyl)phenyl]amino]-2-oxoethyl]-phenylphosphinic acid, 1-methyltridecyl ester | 0.016 |
| 11 | (±)-[2-[[2,6-Bis(1-methylethyl)phenyl]amino]-2-oxoethyl]-phenylphosphinic acid, 1-methylheptyl ester | 0.035 |
| 12 | (±)-[2-[[2,6-Bis(1-methylethyl)phenyl]amino]-2-oxoethyl]-phenylphosphinic acid, dodecyl ester | 0.029 |
| 13 | (±)-[[[[[2,6-Bis(1-methylethyl)phenyl]amino]carbonyl]-amino]methyl]phosphonic acid, ethyl nonyl ester | 0.28 |
| 18 | N-[[[2,6-Bis(1-methylethyl)phenyl]amino]carbonyl]-phosphoramidic acid, diphenyl ester | 0.24 |
| 19 | (±)-[[[2,6-Bis(1-methylethyl)phenyl]amino]carbonyl]-phosphoramidic acid, 4-(hexyloxy)phenyl, phenyl ester | 0.41 |
| 20 | (±)-[[[2,6-Bis(1-methylethyl)phenyl]amino]carbonyl]-phosphoramidic acid, nonyl phenyl ester | 0.062 |
| 22 | (±)-[[[2,6-Bis(1-methylethyl)phenyl]amino]carbonyl]-phosphoramidic acid, 2,6-bis(1-methylethyl)phenyl nonyl ester | 0.055 |
| 24 | N-[[[2,6-Bis(1-methylethyl)phenyl]amino]carbonyl]-phosphoramidic acid, bis(phenylmethyl) ester | 0.16 |
| 25 | (4S-cis)-N-[2,6-Bis(1-methylethyl)phenyl]-N'-(3,4-dimethyl-5-phenyl-1,3,2-oxazaphosphonolidin-2-yl)urea, P-oxide | 0.18 |
| 26 | (±)-N-[[[2,6-Bis(1-methylethyl)phenyl]amino]carbonyl]-P-decylphosphonamidic acid, ethyl ester | 0.11 |
| 27 | (±)-[[[(2,4,6-Trimethoxyphenyl)]amino]carbonyl]amino-phosphoramidic acid, 1-methyltridecyl phenyl ester | 0.063 |

TABLE 1-continued

Biological Activity of Compounds of Formula I

| Example Number | Compound | $IC_{50}$ ($\mu$moles) |
|---|---|---|
| 28 | ($\pm$)-[[[2,6-Bis(1-methylethyl)phenyl]amino]carbonyl]-phosphoramidic acid, 1-methyltridecyl phenyl ester | 0.036 |
| 30 | ($\pm$)-N-[2,6-Bis(1-methylethyl)phenyl]-2-[[5-decyl-3-(phenylmethyl)-1,3,2-oxazaphosphonolidin-2-yl]oxy]acetamide, P-oxide | 0.033 |
| 31 | ($\pm$)-N-[2-[[2,6-Bis(1-methylethyl)phenyl]amino]-2-oxoethyl]-P-phenyl-N-(phenylmethyl)phosphonamidic acid, nonyl ester | 0.023 |
| 32 | ($\pm$)-[2-[[2,6-Bis(1-methylethyl)phenyl]amino]-2-oxoethyl]-(phenylmethyl)phosphoramidic acid, ethyl nonyl ester | 0.014 |
| 33 | ($\pm$)-N-[2-[2,6-Bis(1-methylethyl)phenyl]amino]-2-oxoethyl]phosphoramidic acid, nonyl phenyl ester | |
| 34 | ($\pm$)-[[[2,6-Bis(1-methylethyl)phenyl]amino]-2-oxoethyl]-(phenylmethyl)phosphoramidic acid, nonyl phenyl ester | 0.023 |
| 35 | ($\pm$)-[2-[[2,6-Bis(1-methylethyl)phenyl]amino]-2-oxoethyl]-(phenylmethyl)phosphoramidic acid, 1-methyltridecyl phenyl ester | 0.16 |
| 36 | [2-[[2,6-Bis(1-methylethyl)phenyl]amino]-2-oxoethyl]-phosphonic acid, bis(phenylmethyl)ester | 0.072 |
| 37 | ($\pm$)-P-[2-[[2,6-Bis(1-methylethyl)phenyl]amino]-2-oxoethyl]-N,N-dioctyl phosphonamidic acid, ethyl ester | 0.44 |
| 38 | ($\pm$)-P-[2-[2,6-Bis(1-methylethyl)phenyl]amino]-2-oxoethyl]-N-methyl-N-(2-phenylethyl)-phosphonamidic acid, ethyl ester | 0.31 |

SCHEME I

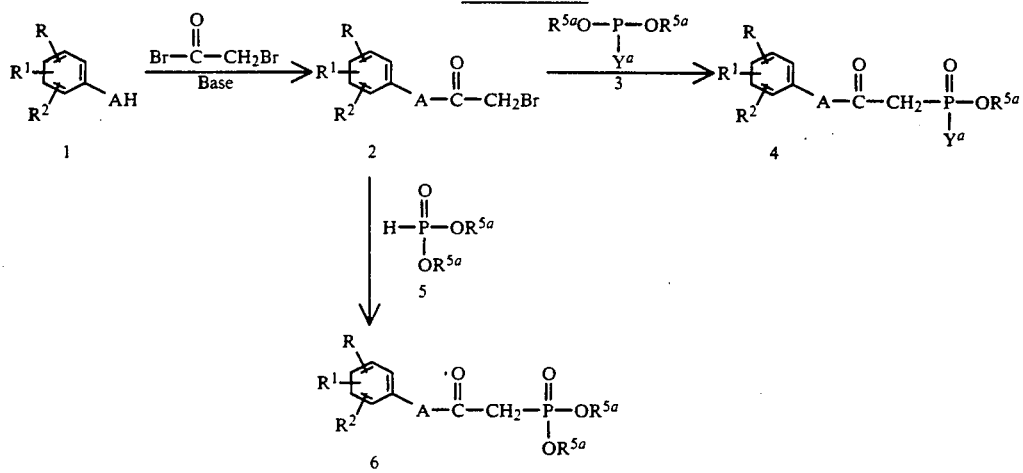

SCHEME II

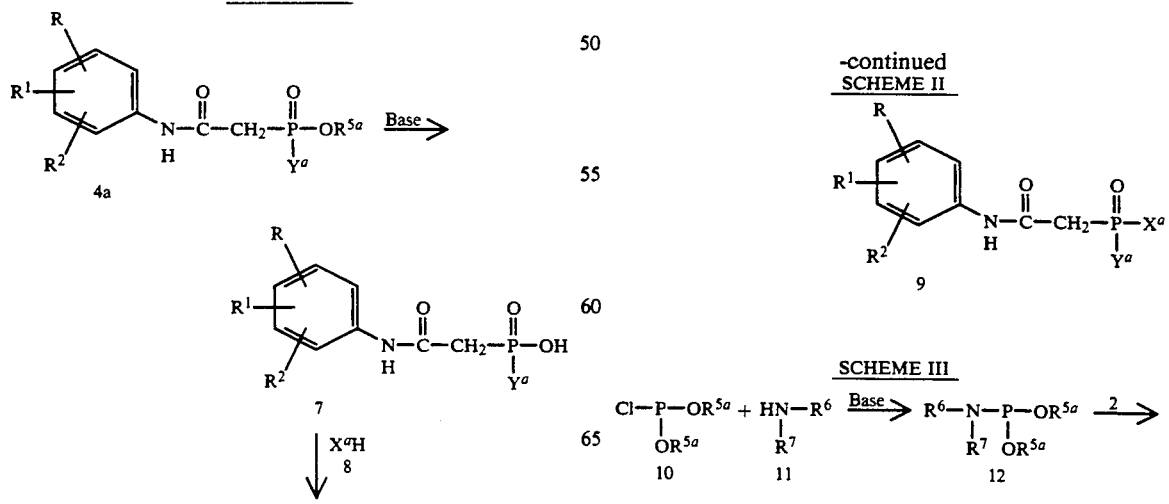

13
-continued
SCHEME III
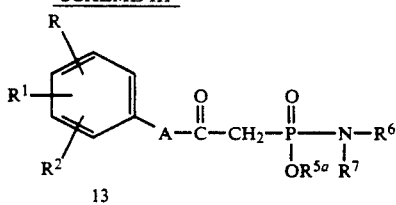
14
-continued
SCHEME V
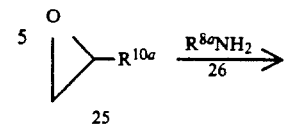
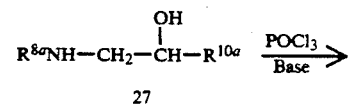
SCHEME IV
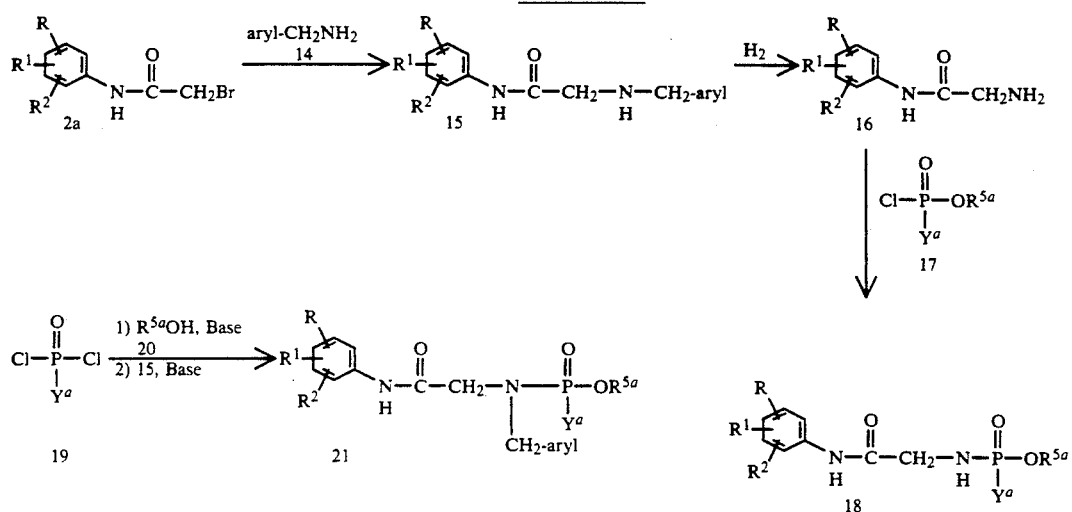
SCHEME V
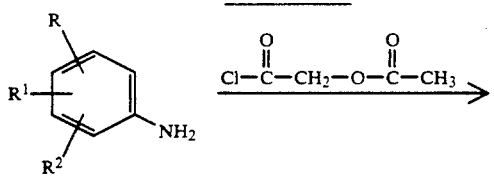
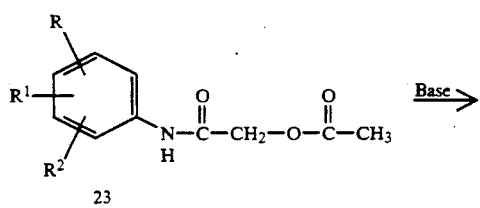
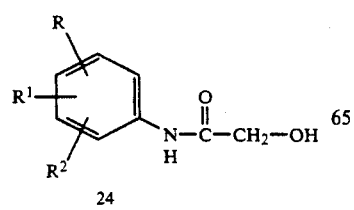
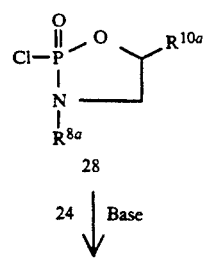

SCHEME VI
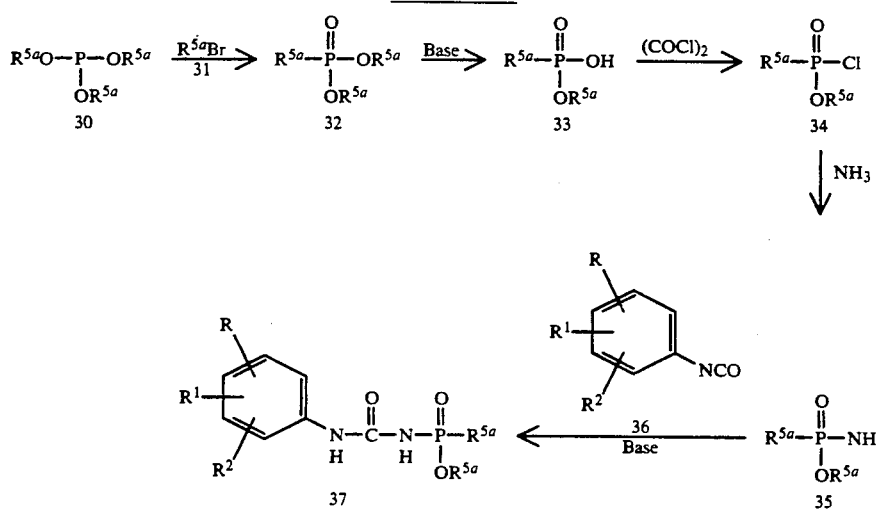
SCHEME VII
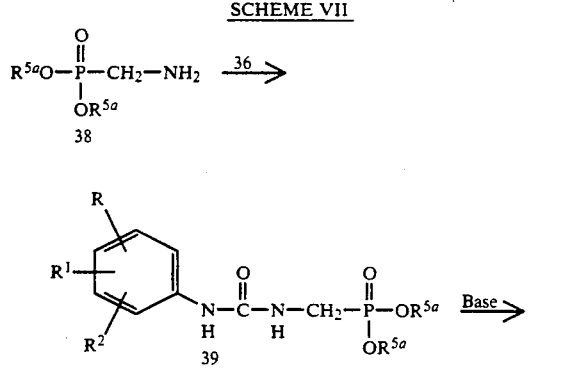
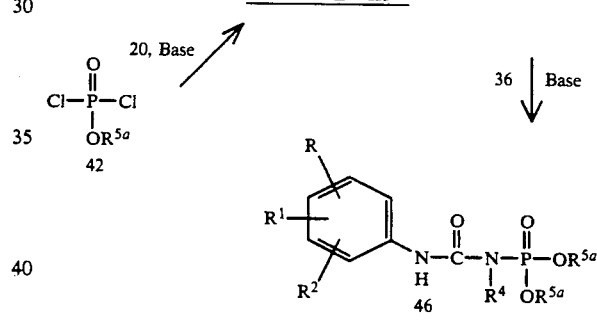
SCHEME VIII
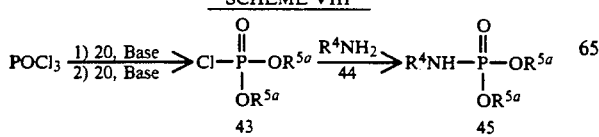
-continued
SCHEME VIII
SCHEME IX
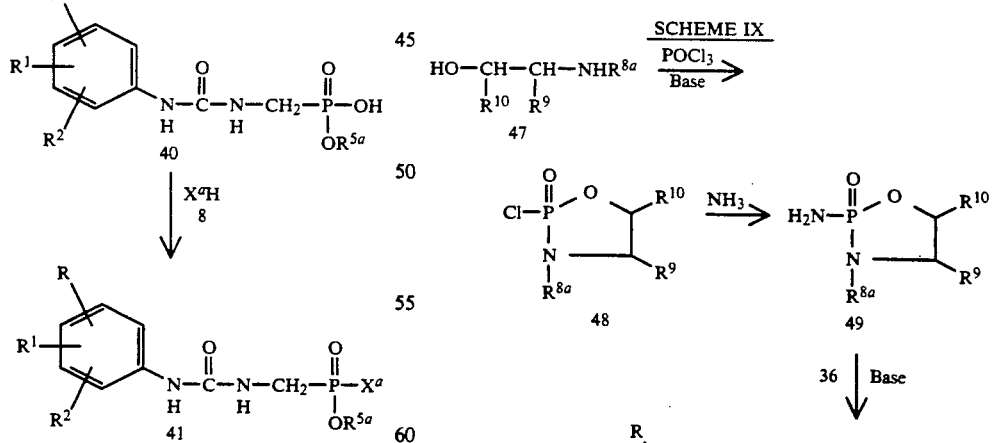
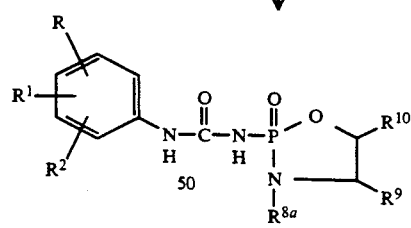

SCHEME X

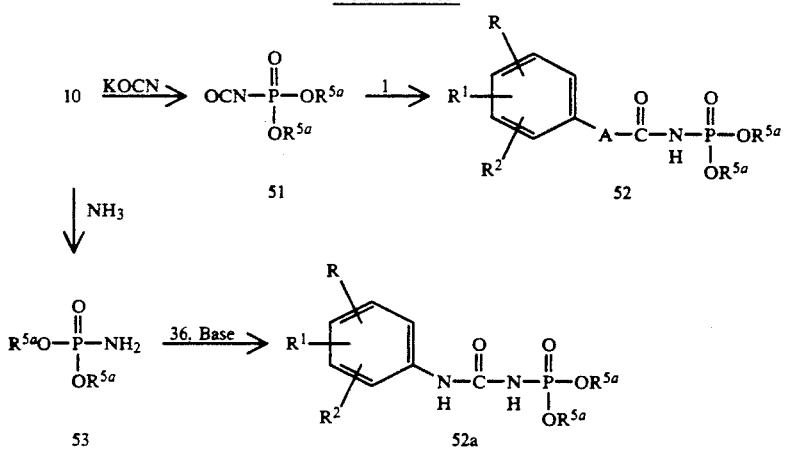

Preferred methods for the preparation of compounds of Formula I are described in Schemes I to X. Compounds of Formula I are designated by numbers 4, 6, 7, 9, 13, 18, 21, 29, 37, 39, 40, 41, 46, 50, 52, and 52a. These schemes illustrate preferred methods from which a person, skilled in the art of organic chemistry, could analogously prepare all compounds of Formula I.

Compounds of Formula I designated 4 and 6 are prepared as outlined in Scheme I. Thus, a compound of Formula 2 wherein R, $R^1$, and $R^2$ are each independently hydrogen, alkyl of from one to six carbon atoms, alkoxy of from one to six carbon atoms, halogen, or trifluoromethyl and A is O or NH is reacted with bromoacetyl bromide in the presence of a base such as, for example, sodium acetate and the like and a solvent such as, for example, acetone and the like to afford a compound of Formula 2 wherein R, $R^1$, $R^2$, and A are as defined above. Reaction of a compound of Formula 2 with a compound of Formula 3 wherein $R^{5a}$ is alkyl of from one to twenty carbon atoms, —$(CH_2)_m$-aryl wherein m is zero or an integer of 1, 2, or 3 or

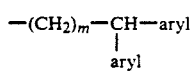

wherein m is as defined above and
$Y^a$ is alkyl of from one to twenty carbon atoms, aryl, or
—$OR^{5a}$ wherein $R^{5a}$ is as defined above
affords a compound of Formula 4 wherein R, $R^1$, $R^2$, A, $R^{5a}$, and $Y^a$ are as defined above. Reactions of a compound of Formula 2 with a compound of Formula 5 wherein $R^{5a}$ is as defined above provided alkyl is not one to four carbon atoms or phenyl in the presence of a base such as, for example, sodium hydride and the like and a solvent such as, for example, tetrahydrofuran and the like affords a compound of Formula 6 wherein R, $R^1$, $R^2$, A, and $R^{5a}$ are as defined above.

Compounds of Formula I designated 7 and 9 are prepared as outlined in Scheme II. Thus, a compound of Formula 4a wherein R, $R^1$, $R^2$, $R^{5a}$, and $Y^a$ are as defined above is treated with a base such as, for example, sodium hydroxide and the like and a solvent such as, for example, aqueous ethanol and the like to afford a compound of Formula 7 wherein R, $R^1$, $R^2$, and $Y^a$ are as defined above. Reactions of a compound of Formula 7 with a compound of Formula 8 wherein $X^a$ is —$OR^{5a}$ wherein $R^{5a}$ is as defined above or

wherein $R^6$ and R are each independently
hydrogen,
alkyl of from one to twenty carbon atoms,
—$(CH_2)_o$-aryl wherein O is an integer of 1, 2, or 3, or

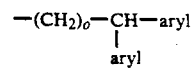

wherein O is as defined above provided both $X^a$ and $Y^a$ are not $OR^{5a}$ wherein $R^{5a}$ is alkyl of from one to four carbon atoms or phenyl in the presence of a coupling reagent such as, for example, dicyclohexylcarbodiimide and the like and 4-dimethylaminopyridine and a solvent such as, for example, pyridine and the like affords a compound of Formula 9 wherein R, $R^1$, $R^2$, $X^a$, and $Y^a$ are as defined above.

A compound of Formula I designated as 13 is prepared as outlined in Scheme III. Thus, a compound of Formula 10 wherein $R^{5a}$ is as defined above is treated with a compound of Formula 11 wherein $R^6$ and $R^7$ are as defined above in the presence of a base such as, for example, triethylamine and the like and a solvent such as, for example, toluene and the like to afford a compound of Formula 12 wherein $R^{5a}$, $R^6$, and $R^7$ are as defined above. Heating a compound of Formula 12 with a compound of Formula 2 affords a compound of Formula 13 wherein R, $R^1$, $R^2$, A, $R^{5a}$, $R^6$, and $R^7$ are as defined above.

Compounds of Formula I designated 18 and 21 are prepared as outlined in Scheme IV. Thus, a compound of Formula 2a wherein R, $R^1$, and $R^2$ are as defined above is reacted with a compound of Formula 15 in the presence of a solvent such as, for example, toluene and the like to afford a compound of Formula 15 wherein R, $R^1$, and $R^2$ are as defined above. Reaction of a compound of Formula 15 in the presence of hydrogen and a catalyst such as, for example, palladium on carbon and the like and a solvent such as, for example, methanol and the like affords a compound of Formula 16 wherein R, $R^1$, and $R^2$ are as defined above. Reaction of a compound of Formula 16 with a compound of Formula 17 wherein $Y^a$ and $R^{5a}$ are as defined above in the presence of a base such as, for example, triethylamine and the like and a solvent such as, for example, tetrahydrofuran and the like affords a compound of Formula 18 wherein R, $R^1$, $R^2$, $Y^a$, and $R^{5a}$ are as defined above. A compound of Formula 19 is reacted first with a compound of Formula 20 wherein $R^{5a}$ is as defined above and a base such as, for example, triethylamine and the like and a solvent such as, for example, toluene and the like followed by reaction with a compound of Formula 15 and a base such as, for example, triethylamine and the like and a solvent such as, for example, tetrahydrofuran and the like to afford a compound of Formula 21 wherein R, $R^1$, $R^2$, $Y^a$, and $R^{5a}$ are as defined above.

A compound of Formula I designated as 29 is prepared as outlined in Scheme V. Thus, a compound of Formula 22 wherein R, $R^1$, and $R^2$ are as defined above is reacted with acetoxyacetyl chloride in a solvent such as, for example, toluene and the like to afford a compound of Formula 23 wherein R, $R^1$, and $R^2$ are as defined above. A compound of Formula 23 is reacted with a base such as, for example, sodium hydroxide and the like and a solvent such as, for example, aqueous methanol and the like to afford a compound of Formula 24 wherein R, $R^1$, and $R^2$ are as defined above. A compound of Formula 25 wherein $R^{10a}$ is alkyl of from one to twenty carbon atoms or aryl is reacted with a compound of Formula 26 wherein $R^{8a}$s alkyl of from one to twenty carbon atoms or —CH$_2$-aryl in the presence of magnesium perchlorate and a solvent such as, for example, acetonitrile and the like to afford a compound of Formula 27 wherein $R^{8a}$ and $R^{10a}$ are as defined above. Reaction of a compound of Formula 27 with phosphorous oxychloride in the presence of a base such as, for example, triethylamine and the like and a solvent such as, for example, tetrahydrofuran and the like affords a compound of Formula 28 wherein $R^{8a}$ and $R^{10a}$ are as defined above. Reaction of a compound of Formula 28 with a compound of Formula 24 in the presence of a base such as, for example, triethylamine and the like and a solvent such as, for example, tetrahydrofuran and the like affords a compound of Formula 29 wherein R, $R^1$, $R^2$, $R^{8a}$, and $R^{10a}$ are as defined above.

A compound of Formula I designated as 37 is prepared as outlined in Scheme VI. Thus, a compound of Formula 30 wherein $R^{5a}$ is as defined above is heated with a compound of Formula 31 wherein $R^{5a}$ is as defined above to afford a compound of Formula 32 wherein $R^{5a}$ is as defined above. Reaction of a compound of Formula 32 with a base such as, for example, sodium hydroxide and the like and a solvent such as, for example, aqueous ethanol affords a compound of Formula 33 wherein $R^{5a}$ is as defined above. Reaction of a compound of Formula 33 with oxalylchloride in the presence of a catalytic amount of dimethylformamide and a solvent such as, for example, dichloromethane and the like affords a compound of Formula 34 wherein $R^{5a}$ is as defined above. Reaction of a compound of Formula 34 with ammonia in the presence of a solvent such as, for example, toluene and the like affords a compound of Formula 35 wherein $R^{5a}$ is as defined above. Reaction of a compound of Formula 35 with a compound of Formula 36 wherein R, $R^1$, and $R^2$ are as defined above in the presence of a base such as, for example, sodium hydride and the like and a solvent such as, for example, tetrahydrofuran and the like affords a compound of Formula 37 wherein R, $R^1$, $R^2$, and $R^{5a}$ are as defined above.

Compounds of Formula I designated as 39, 40, and 41 are prepared as outlined in Scheme VII. Thus, a compound of Formula 38 wherein $R^{5a}$ is as defined above is reacted with a compound of Formula 36 in the presence of a solvent such as, for example, ethyl acetate and the like to afford a compound of Formula 39 wherein R, R , $R^2$, and $R^{5a}$ are as defined above. Reaction of a compound of Formula 39 with a base such as, for example, sodium hydroxide and the like and a solvent such as, for example, aqueous ethanol affords a compound of Formula 40 wherein R, $R^1$, $R^2$, and $R^{5a}$ are as defined above. Reaction of a compound of Formula 40 with a compound of Formula 8 using the procedure described for preparing a compound of Formula 9 from a compound of Formula 8 affords a compound of Formula 41 wherein R, R1, R , $X^a$, and $R^{5a}$ are as defined above.

A compound of Formula I designated as 46 is prepared as outlined in Scheme VIII. Thus, a compound of Formula 20 is reacted with phosphorus oxychloride in the presence of a base such as, for example, triethylamine and the like and a solvent such as, for example, toluene and the like followed by reaction with a compound of Formula 20 wherein the $R^{5a}$ group in the compounds of Formula 20 are not identical to afford a compound of Formula 43 in which $R^{5a}$ is as defined above with the proviso that the two $R^{5a}$ groups are not the same. Alternatively, a compound of Formula 42 may be reacted with a compound of Formula 20 as described above to afford a compound of Formula 43. Reaction of a compound of Formula 43 with a compound of Formula 44 wherein $R^4$ is hydrogen, alkyl of from one to six carbon atoms or —CH$_2$-aryl affords a compound of Formula 45 wherein $R^4$ is as defined above and the two $R^{5a}$ groups are as defined above but are not the same. Reaction of a compound of Formula 45 with a compound of Formula 36 in the presence of a base such as, for example, sodium hydride and the like and a solvent such as, for example, tetrahydrofuran and the like affords a compound of Formula 46 wherein R, $R^1$, $R^2$, $R^4$, and $R^{5a}$ are as defined above with the proviso that the two $R^{5a}$ groups are not the same and further provided when $R^{5a}$ is alkyl of from one to twenty carbon atoms $R^4$ is hydrogen or —CH$_2$-aryl.

A compound of Formula I designated as 50 is prepared as outlined in Scheme IX. Thus, a compound of Formula 47 wherein $R^9$ and $R^{10}$ are each independently hydrogen, alkyl of from one to twenty carbon atoms or aryl and $R^{8a}$ is as defined above is reacted with phosphorus oxychloride in the presence of a base such as, for example, triethylamine and the like and a solvent such as, for example, toluene and the like to afford a compound of Formula 48 wherein $R^{8a}$, $R^9$, and $R^{10}$ are as defined above. Reaction of a compound of Formula 48 with ammonia in the presence of a solvent such as, for example, toluene and the like affords a compound of Formula 49 wherein $R^{8a}$, $R^9$, and $R^{10}$ are as defined above. Reaction of a compound of Formula 49 with a compound of Formula 36 in the presence of a base such as, for example, sodium hydride and the like and a solvent such as, for example, tetrahydrofuran and the like affords a compound of Formula 50 wherein R, $R^1$, $R^2$, $R^{8a}$, $R^9$, and $R^{10}$ are as defined above.

Compounds of Formula I designated as 52 and 52a are prepared as outlined in Scheme X. Thus, a compound of Formula 10 is heated with potassium cyanate in a solvent such as, for example, acetone and the like to afford a compound of Formula 51 wherein $R^{5a}$ is as defined above. Reaction of a compound of Formula 51 with a compound of Formula 1 affords a compound of Formula 52 wherein R, $R^1$, $R^2$, A, and $R^{5a}$ are as defined above. Reaction of a compound of Formula 10 with ammonia in the presence of a solvent such as, for example, toluene and the like affords a compound of Formula 53 wherein $R^{5a}$ is as defined above. Reaction of a compound of Formula 53 with a compound of Formula 36 in the presence of a base such as, for example, sodium hydride and the like and a solvent such as, for example, tetrahydrofuran and the like affords a compound of Formula 52a wherein R, $R^1$, $R^2$, and $R^{5a}$ are as defined above.

Compounds of Formulas 1, 3, 5, 8, 10, 11, 14, 17, 19, 20, 22, 25, 26, 30, 31, 36, 38, 42, and 47 are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted shortly before use to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 50 mg to 1500 mg preferably 200 mg to 500 mg according to the particular application and the potency of the active component. The composition can, if desired, also contain other compatible therapeutic agents.

The dosage range for a 70-kg mammal is from about 1 mg/kg to about 100 mg/kg of body weight per day or preferably about 3 mg/kg to about 15 mg/kg of body weight per day when the compounds of the present invention are used therapeutically as antihypercholesterolemic and antiatherosclerotic agents. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

(±)-[2-[[2,6-Bis(1-methylethyl)phenyl]amino]2-oxoethyl]phenylphosphinic Acid, Ethyl Ester Diethylphenyl phosphonite (1.2 mL, 6.0 mmol) is added to N-[2,6-bis(1-methylethyl)phenyl]-2-bromoacetamide (Example T) (1.2 mL, 6.0 mmol). The resulting suspension is heated slowly to 150° C. and stirred for 3 hours. The liberated ethyl bromide is removed by short-path distillation. After cooling, flash chromatography (3:1 ethyl acetate/hexane) affords the title compound as a white solid; mp 170°-173° C.

EXAMPLE 2

N-2,6-Bis(1-methylethyl)phenyl-2-(diphenylphosphinyl)acetamide

In a process analogous to Example 1, using methyldiphenyl phosphinite in place of diethyl phenyl phosphonite the title compound is obtained as a white powder; mp 210°–212° C.

EXAMPLE 3

(±)-2-Oxo-2-[2,4,6-trimethoxyphenyl)amino]ethyl]-phenylphosphinic Acid, Ethyl Ester In a process analogous to Example 1, using N-(2,4,6-trimethoxyphenyl)-2-bromoacetamide (Example U) in place of N-[2,6-bis(1-methylethyl)phenyl]-2-bromoacetamide, the title compound is obtained as a white solid; mp 118°–120° C.

EXAMPLE 4

(±)-[2-(2,4-Difluorophenyl)amino]-2-oxoethyl]phenylphosphinic Acid, Ethyl Ester

In a process analogous to Example 1 using N-(2,4-difluorophenyl)-2-bromoacetamide (Example R) in place of N-[2,6-bis(1-methylethyl)phenyl]-2-bromoacetamide, the title compound is obtained as a white solid; mp 144°–145° C.

EXAMPLE 5

(±)-[2-[[2,6-Bis(1-methylethyl)phenyl]amino]-2-oxoethyl]phosphonic Acid, Ethyl Ester Step A: Preparation of
[2-[[2,6-Bis(1-methylethyl)phenyl]amino]-2-oxoethyl]-phosphonic Acid, Diethyl Ester In a process analogous to Example 1, using triethyl phosphite in place of diethylphenyl phosphonite, the title compound is obtained; mp 119°–120° C.

Step B: Preparation of
(±)-2-[[2,6-Bis(1-methylethyl)phenyl]amino]-2-oxoethyl]phosphonic Acid, Ethyl Ester To a solution of [2-[[2,6-bis(1-methylethyl)phenyl]amino]-2-oxoethyl]phosphonic acid, diethyl ester (3.0 g, 8.4 mmol) in ethanol (10 mL) is added 2M sodium hydroxide (12.7 mL, 25.3 mmol). The solution is stirred for 18 hours at room temperature. The solution is diluted with water and chloroform. The aqueous phase is acidified to pH 1 with a 10% aqueous solution of hydrochloric acid, then extracted three times with chloroform. The combined organic extracts are washed with brine, dried over magnesium sulfate, and concentrated to afford 2.7 g of the title compound as a white foam; mp 162°–165° C.

EXAMPLE 6

(±)-[2-[2,6-Bis(1-methylethyl)phenyl]amino]-2-oxoethyl]phenylphosphinic Acid

35 In a process analogous to Example 5, using (±)-[2-[2,6-bis(1-methylethyl)phenyl]amino]-2-oxoethyl] phenylphosphinic acid, ethyl ester in place of [2-[[2,6-bis(1-methylethyl)phenyl]amino]-2-oxoethyl]phosphonic acid, diethyl ester, the title compound is obtained as the monohydrate; mp 85°–102° C.

EXAMPLE 7

(±)-2-[[2,6-Bis(1-methylethyl)phenyl]amino]-2-oxoethyl]phosphonic Acid, Ethyl Nonyl Ester To a solution of (±)-[2-[[2,6-bis(1-methylethyl)-phenyl]amino]-2-oxoethyl]phosphonic acid, ethyl ester (Example 5) (2.0 g, 6.1 mmol) in pyridine (12 mL) at 0° C. is added 1-nonanol (0.88 g, 6.1 mmol) followed by dicyclohexylcarbodiimide (DCC) (1.9 g, 9.2 mmol) and 4-(dimethylamino)pyridine (0.1 g). The mixture is stirred at 0° C. for 30 minutes, then warmed to room temperature and stirred for 72 hours. The mixture is diluted with water and chloroform and filtered. The aqueous phase is extracted three times with chloroform. The combined organic extracts are washed with brine, dried over magnesium sulfate, and concentrated. Flash chromatography (3:2 ethyl acetate/hexane) affords a semisolid which is taken up in hexane and filtered to remove dicyclohexylurea. Concentration of the filtrate affords 1.9 g of the title compound as a colorless liquid; infrared spectroscopy (IR) (chloroform ($CHCl_3$)): 2929, 1682, 1024 $cm^{-1}$; nuclear magnetic resonance spectroscopy ($^1H$ NMR) (250 MHz, deuterated chloroform ($CDCl_3$))$\delta$8.16 (br s, 1 H), 7.33–7.10 (m, 3 H), 4.26–4.05 (m, 4 H), 3.12 (m, 2 H), 3.06 (d, J=20 Hz, 2 H), 1.70 (m, 2 H), 1.37 (t, J=7 Hz, 3 H), 1.40–1.10 (m, 12 H), 1.20 (d, J=7 Hz, 12 H), 0.88 (t, J=7 Hz, 3 H); Mass spectrum, m/e (relative intensity) 454 (15), 453 (28), 435 (44), 3.10 (19), 199 (54), 186 (68), 177 (53), 162 (100), 125 (53), 97 (40).

EXAMPLE 8

(±)-2-[[2,6-Bis(1-methylethyl)phenyl]amino]-2-oxoethyl]-N-(diphenylmethyl)phosphonamidic Acid, Ethyl Ester In a process analogous to Example 7, using benzhydrylamine in place of 1-nonanol, and methylene chloride as solvent in place of pyridine, the title compound is obtained; mp 193°–199° C.

EXAMPLE 9

(±)-2-[[2,6-Bis(1-methylethyl)phenyl]amino]-2-oxoethyl]-N,N-bis(phenylmethyl)phosphonamidic Acid, Ethyl Ester In a process analogous to Example 7, using dibenzylamine in place of 1-nonanol, and methylene chloride in place of pyridine, the title compound is obtained; mp 128°–129° C.

EXAMPLE 10

(±)-2-[[2,6-Bis(1-methylethyl)phenyl]amino2-oxoethyl]phenylphosphinic Acid, 1-Methyltridecyl Ester In a process analogous to Example 7, using (±)-[2-[[2,6-bis(1-methylethyl)phenyl]amino]-2-oxoethyl]-phenylphosphinic acid in place of 25 (±)-[2-[[2,6-bis(1-methylethyl)phenyl]amino]-2-oxoethyl]phosphonic acid, ethyl ester and 2-tetradecanol in place of 1-nonanol, the title compound is obtained as a light yellow oil; IR (film) 3232, 2962, 2925, 2855, 1684, 1522, 1467, 1217, 987, 968 $cm^{-1}$; $^1H$ NMR (250 MHz, $CDCl_3$) (mixture of diastereomers) 8.47 (br s, 1 H), 7.88 (dd, J=13 and 8 Hz, 2 H), 7.64 7.45 (m, 3 H), 7.30–7.10 (m, 3 H), 4.55–4.30 (m, 1H), 3.40–3.11 (m, 2 H), 3.35–2.60 (m, 2 H), 1.95–0.90 (m, 28 H), 1.16 (d, J=7 Hz, 12 H), 0.88 (t, J=7 Hz, 3 H); Mass spectrum, m/e (relative intensity) 556 (9), 555 (9), 388 (15), 360 (92), 342 (11), 201 (100), 177 (36), 157 (40), 141 (21), 111 (17), 97 (29).

EXAMPLE 11

(±)-2-[2,6-Bis(1-methylethyl)phenyl]amino]-2-oxoethyl]phenylphosphinic Acid, 1-Methylheptyl Ester In a process analogous to Example 7, using (±)-[2-[[2,6-bis(1 methylethyl)phenyl]amino]-2-oxoethyl]phenyl phosphinic acid in place of (±)-[2-[[2,6-bis(1-methylethyl)phenyl]amino]-2-oxoethyl phosphonic acid, ethyl ester and 2-octanol in place of 1-nonanol, the title compound is obtained as a white solid; mp 110°–112° C.

EXAMPLE 12

(±)-[2-[[2,6-Bis(1-methylethyl)phenyl]amino]-2-oxoethyl]phenylphosphinic Acid, Dodecyl Ester In a process analogous to Example 7, using (±)-[2-[[2,6-bis(1-methylethyl)phenyl]amino]-2-oxoethyl]phenyl phosphinic acid in place of (±)-[2-[[2,6-bis(1-methylethyl)phenyl]amino]-2-oxoethyl]phosphonic acid, ethyl ester and 1-dodecanol in place of 1-nonanol, the title compound is obtained as a sticky white solid; mp 66°–68° C.

EXAMPLE 13

(±)-[[[[[2,6-Bis(1-methylethyl)phenyl]amino]carbonyl]amino]methyl]phosphonic Acid, Ethyl Nonyl Ester In a process analogous to Example 7, using [[[[[2,6 bis(1-methylethyl)phenyl]amino]carbonyl]-amino]methyl]phosphonic acid, ethyl ester (Example M) in place of (±)-[2-[[2,6-bis(1-methylethyl)phenyl]-amino]-2-oxoethyl]phosphonic acid, ethyl ester, the title compound is obtained as a sticky white solid; mp 66°–70° C.

EXAMPLE 14

(±)-[[[2,6-Bis(1-methylethyl)phenyl]amino]carbonyl]amino]methyl]phosphonic Acid, Ethyl Diphenylmethyl Ester In a process analogous to Example 13, using benzhydrol instead of 1-nonanol, the title compound is obtained as a white solid; mp 129°–131° C.

EXAMPLE 15

(±)-[2-[[2,6-Bis(1 methylethyl)phenyl]amino]-2-oxoethyl]-N-(2,2-diphenylethyl)phosphonamidic Acid, Ethyl Ester To a solution of 2,2-diphenylethylamine (0.45 g, 2.3 mmol) and triethylamine (0.35 mL, 2.5 mmol) in methylene chloride (10 mL) is added 1-(3-dimethylaminopropyl)-3-ethylcarbodiimide hydrochloride (EDCI) (0.48 g, 2.5 mmol), followed by (±)-[2-[[2,6-bis(1-methylethyl)phenyl]amino]-2-oxoethyl]phosphonic acid, ethyl ester (Example 5) (0.74 g, 2.3 mmol). 4-Dimethylaminopyridine (DMAP) (0.1 g) is added and the solution is stirred for 48 hours at room temperature. Additional portions of triethylamine (0.1 mL) and EDCI (0.1 g) are added and stirring is continued for another 24 hours. The reaction mixture is diluted with methylene chloride, washed with water, brine, dried over magnesium sulfate, and concentrated. Flash chromatography (ethyl acetate) affords 0.22 g of the product as a white solid. Recrystallization from ethyl acetate/hexane affords 0.18 g of the title compound as a white solid; mp 172°–176° C.

EXAMPLE 16

N-[[[2,6-Bis(1-methylethyl)phenyl]amino1carbonyl]-phosphoramidic Acid, Diethyl Ester To a suspension of potassium cyanate (0.82 g, 10.1 mmol) in acetone (10 mL) is added diethyl chlorophosphate (1.3 mL, 9.2 mmol). The mixture is heated at reflux for 90 minutes. After cooling to room temperature, 2,6-diisopropylaniline (1.7 mL, 9.2 mmol) is added. The mixture is stirred at room temperature for 2 hours, then heated at reflux for 2 hours. After cooling, the mixture is filtered. The filtrate is diluted with ethyl acetate, washed twice with brine, dried over magnesium sulfate, and concentrated. Flash chromatography (3:2 ethyl acetate/hexane) provides 1.3 g of the product as a white solid. Recrystallization from ethyl acetate/hexane provides an analytical sample; mp 157°–158° C.

EXAMPLE 17

(Diphenoxyphosphinyl)carbamic Acid, 2,6-Bis(1-methylethyl)phenyl Ester

In a process analogous to Example 16, using 2,6-diisopropylphenol in place of 2,6-diisopropylaniline, and diphenyl chlorophosphate in place of diethyl chlorophosphate, the title compound is obtained as a white solid; mp 132°–135° C.

EXAMPLE 18

N-[[[2,6-Bis(1-methylethyl)phenyl]amino]carbonyl]-phosphoramidic Acid, Diphenyl Ester To a suspension of diphenyl phosphoramidate (2.0 g, 8.0 mmol) in tetrahydrofuran (20 mL) at 0° C. is added 2,6-diisopropylphenyl isocyanate (1.7 mL, 8.0 mmol). Sodium hydride (0.32 g, 8.0 mmol) is then added portionwise over 15 minutes. The mixture is allowed to warm to room temperature and stirred for 6 hours. The mixture is partitioned between ethyl acetate and water and the aqueous phase is extracted three times with ethyl acetate. The combined organic extracts are washed with brine, dried over magnesium sulfate, and concentrated. Flash chromatography (7:3 hexane/ethyl acetate) affords 2.4 g of a white solid which is recrystallized (ethyl acetate/hexane) to afford 1.6 g of the title compound as a white solid; mp 171°–175° C.

EXAMPLE 19

(±)-[[[2,6-Bis(1-methylethyl)phenyl]amino]carbonyl]-phosphoramidic Acid, 4-(Hexyloxy)phenyl Phenyl Ester In a process analogous to Example 18, using (±)-4-(hexyloxy)phenyl phenyl phosphoramidic acid (Example A) in place of diphenyl phosphoramidate, the title compound is obtained as a white solid; mp 125°–127° C.

EXAMPLE 20

(±)-[[[2,6-Bis(1-methylethyl)phenyl]amino]carbonyl]-phosphoramidic Acid, Nonyl Phenyl Ester In a process analogous to Example 18, using (±)-phenyl nonyl phosphoramidic acid (Example C) in place of diphenyl phosphoramidate, the title compound is obtained as a white solid; mp 108°–112° C.

EXAMPLE 21

(±)-[[[2,6-Bis(1-methylethyl)phenyl]amino]carbonyl](phenylmethyl)phosphoramidic Acid, Nonyl Phenyl Ester In a process analogous to Example 18, using (±)-N-benzyl phenyl nonyl phosphoramidic acid (Example D) in place of diphenyl phosphoramidate, the title compound is obtained as a colorless oil; IR (film) 3276, 2961, 2928, 1701, 1526, 1288, 1025, 937 cm$^{-1}$; $^1$H NMR (250 MHz, CDCl$_3$)δ9.12 (s, 1 H), 7.44–7.00 (m, 13 H), 5.04 (dd, J=15 and 11 Hz, 1H), 4.65 (dd, J=15 and 11 Hz, 1 H), 4.14 (m, 1 H), 3.89 (m, 1 H), 3.09 (m, 1 H), 2.82 (m, 1 H), 1.65–1.45 (m, 2 H), 1.20–1.00 (m, 24 H), 0.89 (t, J=7 Hz, 3 H); Mass spectrum, m/e (relative intensity) 593 (21), 592 (20), 549 (26), 423 (6), 292 (100), 277 (28), 264 (20), 203 (26), 188 (29), 176 (11), 91 (70).

EXAMPLE 22

(±)-[[[2,6-Bis(1-methylethyl)phenyl]amino]carbonyl]phosphoramidic Acid, 2,6-bis(1-methylethyl)phenyl Nonyl Ester In a process analogous to Example 18, using (±)-[2,6-bis(1-methylethyl)phenyl]nonyl phosphoramidic acid (Example F) in place of diphenyl phosphoramidate, the title compound is obtained as a waxy, white solid; mp 73°–78° C.

EXAMPLE 23

(±)-[[[2,6-Bis(1-methylethyl)phenyl]amino]carbonyl]methyl]phosphoramidic Acid, 2,6-Bis(1-methylethyl)phenyl Nonyl Ester In a process analogous to Example 18, using (±) N-methyl-[2,6-bis(1-methylethyl)phenyl]nonyl phosphoramidic acid (Example G) in place of diphenyl phosphoramidate, the title compound is obtained as a colorless oil; IR (film) 3280, 2962, 2929, 1705, 1526, 1294, 959 cm$^{-1}$; $^1$H NMR (250 MHz, CDCl$_3$)δ9.25 (s, 1 H), 7.27–7.02 (m, 6 H), 4.20–4.00 (m, 2 H), 3.47 (m, 2 H), 3.21 (d, J=7 Hz, 3 H), 3.20–3.03 (m, 2 H), 1.85–1.70 (m, 2 H), 1.50–1.10 (m, 36 H), 0.89 (t, J=7 Hz, 3 H); Mass spectrum, m/e (relative intensity) 602 (36), 601 (97), 600 (44), 423 (10), 398 (35), 310 (46), 264 (12), 217 (70), 204 (100), 178 (33), 162 (26), 149 (20).

EXAMPLE 24

N-[[[2,6-Bis(1-methylethyl)phenyl]amino1carbonyl]phosphoramidic Acid, Bis(phenylmethyl)ester In a process analogous to Example 18, using dibenzyl phosphoramidate instead of diphenyl phosphoramidate, the title compound is obtained as a white powder; mp 136°–138° C.

EXAMPLE 25

(4S-cis)-N-[2,6-Bis(1-methylethyl)phenyl]-N'-(3,4-dimethyl-5-phenyl-1,3,2-oxazaphosphonolidin-2-yl)urea, P-oxide In a process analogous to Example 18, using (4S-cis)-2-amino-3,4-dimethyl-5-phenyl-1,3,2-oxazaphospholidine-2-oxide (Example H) in place of diphenyl phosphoramidate, the title compound is obtained as a white solid; mp 189°–190° C.

EXAMPLE 26

(±)-N-[[[2,6-Bis(1-methylethyl)phenyl]amino]carbonyl]-P-decylphosphonamidic Acid, Ethyl Ester In a process analogous to Example 18, using P-decylphosphonamidic acid, ethyl ester (Example L) in place of diphenyl phosphoramidate, the title compound is obtained as a colorless oil; IR (film) 3246, 2961, 2928, 2856, 1715, 1522, 1458, 1172, 1039 cm$^{-1}$; $^1$H NMR (250 MHz, CDCl$_3$)δ8.38 (br s, 1 H), 7.30–7.00 (m, 3 H), 6.60 (br s, 1 H), 4.30–4.00 (m, 2 H), 3.30–2.95 (m, 2 H), 2.00–1.83 (m, 2 H), 1.80 1.50 (m, 2 H), 1.50–1.10 (m, 29 H), 0.88 (t, J=7 Hz, 3 H); Mass spectrum, m/e (relative intensity) 454 (42), 453 (100), 381 (17), 276 (17), 251 (85), 223 (80), 203 (70), 177 (67), 162 (65).

EXAMPLE 27

(±)-[[[(2,4,6-Trimethoxyphenyl)amino]carbonyl]amino]phosphoramidic Acid, 1-Methyltridecyl Phenyl Ester In a process analogous to Example 18, using (±)-1-methyl tridecyl phenyl phosphoramidic acid (Example S) in place of diphenyl phosphoramidate, and 2,4,6-trimethoxyphenylisocyanate in place of 2,6-diisopropyl phenyl isocyanate, the title compound is obtained as a light yellow oil; IR (film) 3298, 2920, 2853, 1724, 1695, 1596, 1491, 1206, 950 cm$^{-1}$; $^1$H NMR (250 MHz, CDCl$_3$)δ7.38–7.10 (m, 6 H), 6.17 (m, 1 H), 6.11 (s, 2 H), 4.76 (m, 1 H), 3.80 (s, 3 H), 3.75 (s, 6 H), 1.85–1.50 (m, 4 H), 1.45–1.15 (m, 23 H), 0.88 (t, J=7 Hz, 3 H); Mass spectrum; m/e (relative intensity) 579 (7), 578 (6), 405 (4), 383 (29), 289 (4), 222 (2), 209 (100).

EXAMPLE 28

(±)-[[[2,6-Bis(1-methylethyl)phenyl]amino]carbonyl]phosphoramidic Acid, 1-Methyltridecyl Phenyl Ester In a process analogous to Example 18, using (±)-1-methyltridecyl phenyl phosphoramidic acid in place of diphenyl phosphoramidate, the title compound is obtained as a thick oil; IR (film) 3271, 3061, 2958, 1725, 1686, 1528, 1491, 1212, 1024, 954 cm$^{-1}$; $^1$H NMR (250 MHz, CDCl$_3$) (mixture of diastereomers)δ8.33 (br s, $^1$H), 7.40–7.05 (m, 8 H), 6.92 (br s, $^1$H), 4.79 (m, $^1$H), 3.30–2.70 (m, 2 H}, 1.80–1.50 (m, 2 H), 1.44 (d, J=6 Hz, 3/2 H), 1.40 (d, J=6 Hz, 3 H), 1.40–1.00 (m, 32 H), 0.88 (t, J=7 Hz, 3 H); Mass spectrum, m/e (relative intensity) 574 (6), 573 (2), 399 (6), 377 (58), 283 (9), 203 (100).

EXAMPLE 29

[[[[[2,6-Bis(1-methylethyl)phenyl]amino]carbonyl]amino]methyl]phosphonic Acid, Diethyl Ester To a solution of diethyl aminomethyl phosphonate (2.7 g, 16.2 mmol) in ethyl acetate at 0° C. is added dropwise 2,6-diisopropylphenyl isocyanate (3.5 mL, 16.2 mmol). The solution is allowed to warm to room temperature and stirred overnight. After concentration the residue is purified by flash chromatography (ethyl acetate) to afford 5.5 g of material which is recrystallized from ethyl acetate/hexane to provide 4.6 g of the title compound as a white solid; mp 132°–134° C.

EXAMPLE 30

(±)-N-[2,6-Bis(1-methylethyl)phenyl]2-[[5-decyl-3-(phenylmethyl)-1,3,2-oxazaphosphonolidin-2-yl]-oxy]acetamide, P-oxide To a solution of (±)-2-chloro-5-decyl-3-(phenylmethyl)-1,3,2-oxazaphosphonolidine-2-oxide (Example Q) (0.9 g, 2.4 mmol) in tetrahydrofuran (10 mL) is added triethylamine (0.37 mL, 2.7 mmol), followed by N-[2,6 bis(1 methylethyl)phenyl]-2-hydroxyacetamide (Example O) (0.57 g, 2.4 mmol). The mixture is stirred at room temperature for 48 hours, then filtered and concentrated. Flash chromatography (3:2 hexane/ethyl acetate) provides 0.74 g of the title compound as a semi-solid; IR (film) 3239, 2926, 2856, 1701, 1521, 1457, 1257, 1074 cm$^{-1}$; $^1$H NMR (250 MHz, CDCl$_3$)δ7.86 (br s, 1 H), 7.37–7.10 (m, 8 H), 4.57 (d, J=9 Hz, 2 H), 4.29 (dd, J=15 and 9 Hz, $^1$H), 4.17 (dd, J=15 and 8 Hz, 1 H), 3.29 (m, 1 H), 3.12-2.95 (m, 2 H), 1.90-1.40 (m, 2 H), 1.40-1.10 (m, 28 H), 0.88 (t, J=7 Hz, 3 H); Mass spectrum, m/e (relative intensity) 572 (16), 571 (40), 274 (75), 204 (86), 188 (57), 160 (40), 146 (45), 120 (41), 91 (90), 84 (100).

EXAMPLE 31

(±)-N-[2-[2,6-Bis(1-methylethyl)phenyl]amino]-2-oxo-ethyl]-P-phenyl-N-(phenylmethyl)phosphonamidic Acid, Nonyl Ester To an ice-cooled solution of phenylphosphonic dichloride (1.95 g, 0.01 mol) in dry toluene (20 mL) is added triethylamine (1.01 g, 0.01 mol) followed by nonyl alcohol (1.45 g, 0.01 mol) in dry toluene (20 mL) dropwise. The reaction mixture is stirred for 2 hours in an ice bath and then filtered. To this filtrate are added triethylamine (1.01 g, 0.01 mol) and a solution of N-[2,6-bis(1-methylethyl)]phenyl-2-[(phenylmethyl)amino]acetamide (Example V) (3.24 g, 0.01 mol) in dry tetrahydrofuran (20 mL) and the mixture is stirred at room temperature overnight. The reaction mixture is filtered and concentrated. Flash chromatography and crystallization affords the title compound; IR (KBr) 3212, 2961, 2926, 2868, 2855, 1665, 1513, $^1$H NMR (250 MHz, dimethysulfoxide (DMSO))δ9.15 (1 H, s), 7.90-7.80 (2 H, m), 7.60-7.40 (3 H, m), 7.30-7.00 (8 H, m), 4.42-4.20 (2 H, m), 4.20-4.00 (2 H, m), 3.90-3.60 (2 H, m), 3.10-2.8 (2 H, m), 1.80-1.60 (2 H, m), 1.50-1.18 (12 H, m), 1.08 (12 H, d, J=7 Hz), 0.84 (3 H, t, J=6.5 Hz).

EXAMPLE 32

(±)-[2-[[2,6 Bis(1-methylethyl)phenyl]amino]-2-oxoethyl](phenylmethyl)phosphoramidic Acid, Ethyl Nonyl Ester In a process analogous to Example 34, using ethyl dichlorophosphate in place of phenyldichlorophosphate, the title compound is obtained as a colorless oil; IR (film) 3246, 2960, 2926, 1696, 1232, 1029, 950 cm$^{-1}$; $^1$H NMR (250 MHz, CDCl$_3$)δ7.86 (br s, 1 H), 7.38-7.10 (m, 8 H), 4.35 (dd, J=10 and 3 Hz, 2 H), 4.20-3.95 (m, 4 H), 3.80 (d, J=12 Hz, 2 H), 3.15-2.95 (m, 2 H), 1.75-1.60 (m, 2 H), 1.40-1.15 (m, 27 H), 0.88 (t, J=7 Hz, 3 H); Mass spectrum, m/e (relative intensity) 560 (31), 559 (94), 354 (26), 340 (66), 264 (30), 219 (100), 203 (62), 138 (26), 91 (81).

EXAMPLE 33

(±)-N-[2-[2,6-Bis(1-methylethyl)phenyl]amino]-2-oxo-ethyl]phosphoramidic Acid, Nonyl Phenyl Ester In a process analogous to Example 34, using N-[2,6-bis(1-methylethyl)phenyl]-2-aminoacetamide (Example W) in place of N-[2,6-bis(1-methylethyl)phenyl]-2-(phenylmethyl)aminoacetamide, the title compound is obtained as a white solid; mp 88°-90° C.

EXAMPLE 34

(±)-[[[2,6-Bis(1-methylethyl)phenyl]amino]2-oxoethyl]-(phenylmethyl)phosphoramidic Acid, Nonyl Phenyl Ester To an ice-cooled solution of phenyl dichlorophosphate (2.83 g, 0.02 mol) in dry toluene (50 mL) is added triethylamine (2.02 g, 0.02 mol) followed by nonyl alcohol (2.89 g, 0.02 mol) in dry toluene (40 mL) dropwise. The reaction mixture is stirred in an ice bath for 2 hours and then filtered. To this filtrate are added triethylamine (2.02 g, 0.02 mol) and a solution of N-[2,6-bis(1-methylethyl)phenyl]-2-[phenylmethyl]amino-acetamide (Example V) (6.40 g, 0.02 mole) and the mixture is stirred at room temperature overnight. The reaction mixture is filtered and concentrated. Flash column chromatography and crystallization from ethyl acetate affords 3.8 g of the title compound; IR (KBr); 3285, 2961, 2925, 2858, 2367, 1684, and 1508. $^1$H NMR (250 MHz, DMSO)δ9.22 (1 H, s), 7.44–6.92 (13 H, m), 4.50–4.30 (2 H, m), 4.30–4.00 (2 H, m), 4.00–3.60 (2 H, m), 3.10–2.80 (2 H, m), 1.70–1.40 (2 H, m), 1.4–1.18 (12 H, m), 1.18–1.00 (12 H, d, J=7 Hz), 0.98–0.76 (3 H, m).

EXAMPLE 35

(±)-[2-[[2,6-Bis(1-methylethyl)phenyl]amino]-2-oxoethyl](phenylmethyl)phosphoramidic Acid, 1-Methyltridecyl Phenyl Ester To an ice-cooled solution of phenyl dichlorophosphate (0.98 g, 0.005 mol) in dry toluene (20 mL) is added triethylamine (0.51 g, 0.005 mol) followed by 2-tetradecanol (1.07 g, 0.005 mol). The reaction mixture is allowed to warm to room temperature and stirred at room temperature overnight. The reaction mixture is filtered. To the filtrate are added triethylamine (0.51 g, 0.005 mol) and a solution of N-[2,6-bis(1-methylethyl)-phenyl]-2-[phenylmethyl]amino, acetamide (Example V) (1.49 g, 0.005 mol) in dry tetrahydrofuran (20 mL) and the mixture is stirred overnight. The reaction mixture is filtered and concentrated. Flash column chromatography affords 1.1 g of the title compound as an oil; IR (film), 3255, 2960, 2925, 2855, 1696, 1677, 1491. $^1$H NMR (250 MHz, DMSO)δ9.18 (1 H, s), 7.42-7.00 (13 H, m), 4.75-4.55 (1 H, m), 4.50-4.25 (2 H, m), 4.00-3.50 (2 H, m), 3.10-2.90 (2 H, m), 1.95-1.12 (25 H, m), 1.09 (12 H, d, J=7 Hz), 0.85 (3 H, t, J=6.5 Hz).

EXAMPLE 36

[2-[[2,6-Bis(1-methylethyl)phenyl]amino]-2-oxoethyl]-phosphonic Acid, Bis (Phenylmethyl)ester A solution of sodium dibenzylphosphite is prepared by the addition of a 60% mineral oil dispersion of sodium hydride (0.4 g, 0.01 mol) to a solution of dibenzyl phosphite (2.62 g, 0.01 mol) in dry tetrahydrofuran (20 mL). To the resultant solution is added N-[2,6-bis(1-methylethyl)phenyl]-2-bromoacetamide (2.98 g, 0.01 mol) and the mixture is stirred at 50° C. overnight. The reaction mixture is filtered and concentrated. Flash chromatography and crystallization affords 1.4 g of the title compound; mp 117°–119° C.

EXAMPLE 37

(±)-P-[2-[[2,6-Bis(1-methylethyl)phenyl]amino]-2-oxoethyl]-N,N-dioctyl Phosphonamidic Acid, Ethyl Ester

Step I

To an ice-cooled solution of dioctylamine (2.42 g, 0.01 mol) is added triethylamine (1.01 g, 0.01 mol) followed by diethylchlorophosphite (1.57 g, 0.01 mol) dropwise and the mixture is allowed to stir for 1 hour. The reaction mixture is filtered and concentrated; $^1$H NMR (200 MHz, CDCl$_3$)δ3.9–3.6 (4 H, m), 3.05–2.8 (4 H, m), 1.6–1.00 (30 H, m), 0.92 (6 H, m).

Step II

The crude phosphite (3.25 g) prepared in Step I and N-[2,6-bis(1-methylethyl)phenyl]-2-bromoacetamide (2.68 g, 0.009 mol) are heated slowly to 130° C. under a nitrogen atmosphere. The reaction mixture is stirred at this temperature for 2 hours. The liberated ethyl bromide is removed constantly via a short arm distillation device. The reaction mixture is cooled and flash chromatography affords 0.75 g of the title compound as an oil; IR (KBr); 3221, 3215, 2959, 2926, 2855, 1679, 1522; $^1$H NMR (250 MHz, CDCl$_3$)δ8.50 (1 H, s), 7.38–7.00 (3 H, m), 4.14–4.85 (2 H, m), 3.4–2.7 (8 H, m), 1.90–1.02 (39 H, m), 0.98–0.75 (6 H, m).

EXAMPLE 38

(±)-P-[2-[2,6-Bis(1-methylethyl)phenyl]amino]-2-oxoethyl]-N-methyl-N-(2-phenylethyl)phosphonamidic Acid, Ethyl Ester

Step I

In a process analogous to Step I in Example 37, using N-methyl phenethylamine in place of dioctylamine, the phosphite is obtained.

Step II

In a process analogous to Step II in Example 41, using the phosphite from Step I, affords the title compound as a white solid (0.62 g); mp 140°–142° C.

PREPARATION OF STARTING MATERIALS

EXAMPLE A (±)-4-(Hexyloxy)phenyl Phenyl Phosphoramidic Acid

To a solution of phenylphosphinic dichloride (2.3 g, 10.9 mmol) and triethylamine (1.8 mL, 13.0 mmol) in toluene (15 mL) at 0° C. is added dropwise a solution of 4-(hexyloxy)phenol (2.3 g, 11.8 mmol) in toluene (5 mL). The mixture is allowed to warm slowly to room temperature and stirred for 2 hours. The mixture is filtered. The filtrate is cooled to 0° C. and ammonia is bubbled in for 30 minutes. The mixture is filtered. The precipitate is suspended in chloroform and stirred for 1 hour. The mixture is filtered and the filtrate concentrated to afford 2.6 g of the title compound as a white solid; $^1$H NMR (200 MHz, CDCl$_3$) 7.40–7.10 (m, 7 H), 6.85 (d, J=9 Hz, 2 H), 3.92 (t, J=7 Hz, 2 H), 3.24 (br d, J=6 Hz, 2 H), 1.83–1.65 (m, 3 H), 1.50–1.26 (m, 5 H), 0.91 (t, J=7 Hz, 3 H).

EXAMPLE B (±)-Phenyl Nonyl Phosphoryl Chloride

To a solution of phenylphosphonic dichloride (3.0 g, 14.2 mmol) and triethylamine (2.4 mL, 17.1 mmol) in toluene (20 mL) at 0° C. is added dropwise a solution of 1-nonanol (2.05 g, 14.2 mmol) in toluene (5 mL). The mixture is allowed to warm slowly to room temperature and stirred for 2 hours. The mixture is filtered, and the filtrate is concentrated to afford 4.5 g of the title compound as a light yellow liquid; $^1$H NMR (200 MHz, CDCl$_3$)δ7.40–7.15 (m, 5 H), 4.40–4.25 (m, 2 H), 1.90–1.65 (m, 2 H), 1.45–1.20 (m, 12 H), 0.89 (t, J=7 Hz, 3 H).

EXAMPLE C (±)-Phenyl Nonyl Phosphoramidic Acid

Ammonia is bubbled into a solution of (±)-phenyl nonyl phosphoryl chloride (Example B) (2.5 g, 7.8 mmol) in toluene (20 mL) at 0° C. After 5 minutes, the ice bath is removed and the stream of ammonia is continued for 10 minutes. The mixture is filtered and concentrated to afford 2.2 g of the title compound as a white solid; mp 64°–65° C.

EXAMPLE D (±) N-Benzyl Phenyl Nonyl Phosphoramidic Acid

To a solution of (±) phenyl nonyl phosphoryl chloride (Example C) (2.0 g, 6.3 mmol) in toluene (20 mL) at 0° C. is added a solution of benzylamine (0.67 g, 6.3 mmol) and triethylamine (1.3 mL, 9.4 mmol) in toluene (5 mL) over 5 minutes. The mixture is allowed to warm to room temperature and is stirred for 90 minutes. The mixture is filtered, and the filtrate concentrated. Flash chromatography (3:2 hexane/ethyl acetate) affords 2.1 g of the title compound as a colorless oil; $^1$H NMR (200 MHz, CDCl$_3$)δ 7.40–7.10 (m, 10 H), 4.19 (dd, J=10 and 7 Hz, 2 H), 4.19–4.05 (m, 2 H), 3.20–3.00 (m, 1 H), 1.70–1.60 (m, 2 H), 1.35–1.20 (m, 12 H), 0.89 (t, J=7 Hz, 3 H).

EXAMPLE E (±)-[2,6-Bis(1-methylethyl)phenyl]nonyl Phosphoryl Chloride

To a solution of phosphorus oxychloride (1.53 g, 10.0 mmol) and triethylamine (3.5 mL, 25.0 mmol) in toluene (20 mL) at 0° C. is added dropwise a solution of 2,6-diisopropylphenol (1.78 g, 10.0 mmol) in toluene (5 mL). The mixture is allowed to warm slowly to room temperature and stirred for 2 hours. The mixture is cooled to 0° C., and a solution of 1-nonanol (1.44 g, 10.0 mmol) in toluene (5 mL) is added dropwise. The mixture is allowed to warm to room temperature and stirred for 2 hours. The mixture is filtered and the filtrate concentrated to afford 4.1 g of a crude oil, which is taken up in 1:1 EtOAc/hexane and filtered through a small pad of silica gel. The filtrate is concentrated to afford 3.7 g of a light yellow liquid; $^1$H NMR (200 MHz, CDCl$_3$)δ7.17 (br s, 3 H), 4.30–4.10 (m, 2 H), 3.43 (m, 2 H), 1.85–1.65 (m, 4 H), 1.45–1.10 (m, 10 H), 1.25 (d, J=7 Hz, 12 H), 0.89 (t, J=7 Hz, 3 H).

EXAMPLE F (±)-[2,6-Bis(1-methylethyl)phenyl]nonyl Phosphoramidic Acid

In a process analogous to Example C using (±)-[2,6-bis(1-methylethyl)phenyl]nonyl phosphoryl chloride (Example E) in place of phenyl nonyl phosphoryl chloride, the title compound is obtained as a light yellow liquid; $^1$H NMR (200 MHz, CDCl$_3$) δ7.14 (s, 3 H), 4.09 (q, J=7 Hz, 2 H), 3.50 (m, 2 H), 2.90 (br s, 2 H), 1.90-1.55 (m, 4 H), 1.30-1.10 (m, 10 H), 1.23 (d, J=7 Hz, 12 H), 0.89 (t, J=7 Hz, 3 H).

EXAMPLE G (±)-N-methyl [2,6-bis(1-methylethyl)phenyl]nonyl Phosphoramidic Acid In a process analogous to Example D, using methylamine in place of benzylamine, and (±)-[2,6-bis(1-methylethyl)phenyl nonyl phosphoryl chloride in place of (±)-phenyl nonyl phosphoryl chloride, the title compound is obtained as a colorless oil after flash chromatography (3:2 hexane/ethyl acetate); 1 H NMR (200 MHz, CDCl$_3$) δ7.13 (s, 3 H), 4.05-3.98 (m, 2 H), 3.54 (m, 2 H), 2.72 (dd, J=12 and 5 Hz, 3 H), 2.65 (m, 1 H), 1.70-1.50 (m, 4 H), 1.35-1.15 (m, 10 H), 1.23 (d, J=7 Hz, 12 H), 0.89 (t, J=7 Hz, 3 H).

EXAMPLE H (4S-cis)-2-Amino-3,4-dimethyl-5-phenyl-1,3,2-oxazaphospholidine-2-oxide In a process analogous to Example C, using (4S-cis)-2-chloro-3,4-dimethyl-5-phenyloxazaphospholidine-2-oxide in place of phenyl nonyl phosphoryl chloride, the title compound is obtained as a white solid; mp 170°-172° C.

EXAMPLE I

Diethyl-P-decylphosphonate

In a process analogous to Example 1, using bromodecane instead of N-[2,6-bis(1-methylethyl)phenyl]-2-bromoacetamide, the title compound is obtained after short-path distillation; bp 130°-135° C./0.1 mm.

EXAMPLE J

P-Decylphosphonic Acid, Ethyl Ester

In a process analogous to Example 6, using diethyl decylphosphonate (Example I) instead of [2-[[2,6-bis(1-methylethyl)phenyl]amino]-2-oxoethyl]phosphonic acid, diethyl ester, and heating at reflux for 22 hours instead of room temperature, the title compound is obtained as a colorless oil; $^1$H NMR (200 MHz, CDCl$_3$) 9.30 (br s, $^1$H), 4.15-4.00 (m, 2 H), 1.85-1.50 (m, 4 H), 1.40-1.15 (m, 17 H), 0.88 (t, J=7 Hz, 3 H).

EXAMPLE K

P-Decylphosphonyl Chloride, Ethyl Ester

To a solution of P-decylphosphonic acid, ethyl ester (Example J) (1.2 g, 4.8 mmol) in methylene chloride (10 mL) at 0° C. is added one drop of dimethylformamide. Oxalyl chloride (0.46 mL, 5.3 mmol) is added dropwise. The solution is stirred 30 minutes at 0° C., then warmed to room temperature and stirred for 4 hours. The mixture is concentrated to afford the title compound as a light yellow oil (1.2 g), $^1$H NMR (90 MHz, CDCl$_3$) δ4.40-4.00 (m, 2 H), 2.30-1.15 (m, 21 H), 0.90 (t, J=7 Hz, 3 H).

EXAMPLE L

P-Decylphosphonamidic Acid, Ethyl Ester

In a process analogous to Example C, using P-decylphosphonyl chloride, ethyl ester (Example K) in place of phenyl nonyl phosphoryl chloride, the title compound is obtained as a white solid; 1 H NMR (90 MHz, CDCl$_3$) δ4.05 (p, J=8 Hz, 2 H), 2.90 (br s, 2 H), 1.90-1.10 (m, 21 H), 0.90 (t, J=7 Hz, 3 H).

EXAMPLE M

[[[[[2,6-Bis(1 methylethyl)phenyl]amino]carbonyl]amino]methyl]-phosphonic Acid, Ethyl Ester In a process analogous to Example 6, using [[[[[2,6 bis(1-methylethyl)phenyl]amino]carbonyl]amino]methyl]phosphonic acid, diethyl ester (Example 30) instead of [2-[[2,6-bis(1-methylethyl)phenyl]amino]-2-oxoethyl]phosphonic acid, diethyl ester, the title compound is obtained as a white foam; IR (KBr) 3374, 2968, 1653, 1559, 1200, 1017 cm$^{-1}$; $^1$H NMR (200 MHz, CDCl$_3$) δ7.35-7.05 (m, 3 H), 6.40 (m, 1 H), 4.55 (m, 1 H), 4.20-4.00 (m, 2 H), 3.80-3.60 (m, 2 H), 3.35-3.05 (m, 2 H), 1.35-1.05 (m, 12 H); Mass spectrum, m/e (relative intensity) 343 (3), 250 (12), 204 (100), 188 (11), 177 (10), 135 (8).

EXAMPLE N

N-[2,6-Bis(1-methylethyl)phenyl]-2-acetoxy Acetamide

To a solution of acetoxyacetyl chloride (13.5 g, 98.7 mmol) in toluene (70 mL) at 0° C. is added dropwise via a dropping funnel a solution of 2,6-diisopropylaniline (17.5 g, 98.7 mmol) and triethylamine (20.6 mL, 148.1 mmol) in toluene (20 mL). After completion of the addition, the mixture is allowed to warm to room temperature and stirred for 24 hours. The mixture is filtered through a small pad of silica gel. The filtrate is concentrated to afford 11 g of a brown solid. The precipitate is suspended in ethyl acetate and stirred overnight. After filtration, the filtrate is concentrated to give another 10 g of a brown solid. Recrystallization (ethyl acetate/hexane) of the combined material provided 12 g of the title compound as an off-white solid; mp 179°-182° C.

EXAMPLE O

N-[2,6-Bis(1-methylethyl)phenyl]-2-hydroxyacetamide

To a solution of N-[2,6-bis(1-methylethyl)phenyl]-2-acetoxyacetamide (Example N) (5.7 g, 20.6 mmol) in methanol (50 mL) is added 2M sodium hydroxide solution (20 mL). The solution is stirred at room temperature for 1 hour. The mixture is concentrated, diluted with water, and extracted three times with ethyl acetate. The combined organic extracts are washed with brine, dried over magnesium sulfate, and concentrated to afford 4.6 g of the title compound as an off-white solid; mp 164°-166° C.

EXAMPLE P 1-(N-Benzyl)amino-2-dodecanol

To a solution of 1,2-epoxydodecane (1.84 g, 10.0 mmol) in anhydrous acetonitrile (5 mL) is added anhydrous magnesium perchlorate (2.23 g, 10.0 mmol). After 15 minutes, benzylamine (1.1 mL, 10.0 mmol) is added dropwise and the solution is stirred for 50 hours at room temperature. The mixture is concentrated, diluted with water, and extracted twice with ethyl acetate. The combined organic extracts are washed with water, brine, dried over magnesium sulfate, and concentrated to afford 2.9 g of the title compound as a white solid; $^1$H NMR (200 MHz, CDCl$_3$)δ7.38–7.25 (m, 5 H), 3.87 (d, J=2 Hz, 2 H), 3.80–3.65 (m, 1 H), 3.00–2.75 (m, 3 H), 2.60–2.45 (m, 1 H), 1.40–1.20 (m, 18 H), 0.88 (t, J=7 Hz, 3 H).

EXAMPLE Q (±)-2-Chloro-5-decyl-3-(phenylmethyl)-1,3,2-oxazaphosphonolidine 2-oxide To a solution of 1-(N-benzylamino)-2-dodecanol (Example P) (2.0 g, 6.9 mmol) and triethylamine (3.8 mL) in toluene (20 mL) at 0° C. is added dropwise phosphorus oxychloride (0.64 mL, 6.9 mmol). The mixture is stirred for 2 hours at 0° C., then filtered through silica gel and concentrated to afford 1.9 g of the title compound as a colorless oil; $^1$H NMR (200 MHz, CDCl$_3$) (mixture of diastereomers)δ7.40–7.25 (m, 5 H), 4.70–4.45 (m, 1 H), 4.44 (dd, J=14 and 10 Hz, 1 H), 3.84 (dd, J=14 and 5 Hz, 1 H), 3.40–3.10 (m, 1 H), 2.84 (t, J=8 Hz, 1 H), 1.95–1.10 (m, 18 H), 0.88 (t, J=7 Hz, 3 H).

EXAMPLE R

N-(2,4-Difluorophenyl)-2-bromoacetamide

In a process analogous to Example T, using 2,4-difluoroaniline in place of 2,6-diisopropylaniline, the title compound is obtained as an off-white solid; IR (KBr) 3266, 3083, 1661, 1563, 1501, 1432, 1260, 1143, 1095, 853 cm$^{-1}$; $^1$H NMR (250 MHz, CDCl$_3$)δ8.30 (br s, $^1$H), 8.28–8.15 (m, $^1$H), 6.91 (t, J=9 Hz, 2 H), 4.05 (s, 2 H); Mass spectrum, m/e (relative intensity) 251 (14), 249 (14), 142 (4), 129 (100), 101 (16).

EXAMPLE S (±)-1-Methyl tridecyl phenyl phosphoramidic acid

In a process analogous to Example A, using 2-tetradecanol instead of 4-(hexyloxy)phenol, the title compound is obtained as a white solid; mp 60°–64° C. (mixture of diastereomers).

EXAMPLE T

N-[2,6-Bis(1-methylethyl)phenyl]-2-bromoacetamide

To a well-stirred ice-cooled mixture of 2,6-diisopropylaniline (10.0 g, 0.056 mol) in acetone (25 mL) and water (25 mL) and sodium acetate trihydrate (15.3 g, 0.112 mol), bromoacetyl bromide (17.0 g, 0.084 mol) is added dropwise. The reaction mixture is allowed to warm to room temperature and stirred for 1 hour. The reaction mixture is diluted with water (100 mL), the product filtered, washed with cold water, sodium bicarbonate solution, water, and finally with hexane. The product is dried in a vacuum at 40° C. to afford 14.5 g of the title compound as a white solid; mp 170° C.

EXAMPLE U

N-(2,4,6-Trimethoxyphenyl)-2-bromoacetamide

In a process analogous to Example T using 2,4,6-trimethoxyaniline in place of 2,6-diisopropylaniline, the title compound is obtained as a solid; mp 160°–161° C.

EXAMPLE V

N-2,6-Bis(1-methylethyl)phenyl]-2-(phenylmethyl)amino]acetamide

To a stirred solution of benzylamine (6.43 g, 0.06 mol) in toluene (75 mL) is added N-[2,6-bis(1-methylethyl)phenyl]-2-bromoacetamide (8.95 g, 0.03 mol) and then refluxed for 2 hours. The reaction mixture is filtered and concentrated. Flash column chromatography and crystallization affords 6.4 g of the title compound; $^1$H NMR (250 MHz, CDCl$_3$)δ8.73 (1 H, s , 7.40–7.04 (8 H, m), 3.93 (2 H, s), 3.53 (2 H, s), 3.05–2.95 (2 H, m), 2.00 (1 H, br s , 1.18 12 H, d, J=6.8 Hz).

EXAMPLE W

N-[2,6-Bis(1-methylethyl)phenyl]-2-aminoacetamide

To a solution of N-[2,6-bis(1-methylethyl)phenyl]-2-[(phenylmethyl)amino]acetamide (Example V) (0.80 g, 2.5 mmol) in methanol (10 mL) is added 20% Pd/C (0.1 g). The mixture is stirred under an atmosphere of hydrogen for 20 hours. After filtration and concentration, flash chromatography (ethyl acetate) affords 0.47 g of the title compound as a white solid; mp 88°–95° C.

We claim:

1. A compound of Formula I

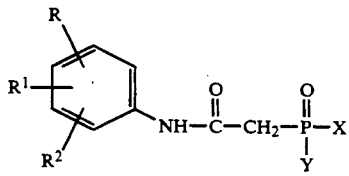

wherein

R, R$^1$ and R$^2$ are each independently hydrogen, alkyl of from one to six carbon atoms, alkoxy of from one to six carbon atoms, halogen, or trifluoromethyl;

X and Y are each independently alkyl of from one to twenty carbon atoms, with the proviso that X and Y are not both alkyl, aryl, —OR$^5$ wherein R$^5$ is alkyl of from one to twenty carbon atoms, —(CH$_2$)$_m$-aryl wherein m is zero or an integer of 1, 2, or 3 or

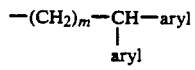

wherein m is as defined above

wherein R$^6$ and R$^7$ are each independently hydrogen, alkyl of from one to twenty carbon atoms, —(CH$_2$)$_o$-aryl wherein O is an integer of 1, 2, or 3 or

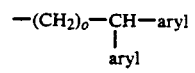

wherein O is as defined above or

X and Y are taken together with the phosphorus atom to which they are attached to form a ring denoted by

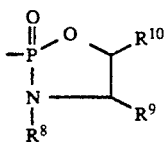

wherein R⁸ is
hydrogen,
alkyl of from one to twenty carbon atoms, or
—CH₂-aryl and
R⁹ and R¹⁰ are each independently hydrogen, alkyl of from one to twenty carbon atoms, or aryl; provided
both X and Y are not —OR⁵ wherein R⁵ is alkyl of from one to six carbon atoms or phenyl; or a pharmaceutically acceptable base addition salt thereof.

2. A compound according to claim 1, in which X and Y are each independently
aryl,
—OR⁵ wherein R⁵ is
  alkyl of from one to twenty carbon atoms, with the proviso that X and Y are not both alkyl,
  —(CH₂)ₘ-aryl wherein m is zero or an integer of 1, 2, or 3, or

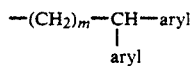

wherein m is as defined above,

wherein R⁶ and R⁷ are each independently
  hydrogen,
  alkyl of from one to fifteen carbon atoms,
  —(CH₂)ₒ-aryl wherein O is an integer of 1 or 2,

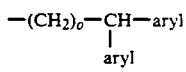

wherein O is zero or an integer of 1 or
X and Y are taken together with the phosphorus atom to which they are attached to form a ring denoted by

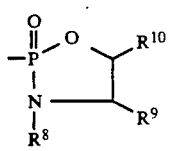

wherein R⁸ is alkyl of from one to six carbon atoms or
—CH₂-aryl and R⁹ and R¹⁰ are each independently
hydrogen,
alkyl of from one to fifteen carbon atoms or
aryl; provided both X and Y are not —OR⁵
wherein R⁵ is alkyl of from one to six carbon atoms or phenyl.

3. A compound according to claim 2, in which X and Y are each independently
aryl,
—OR⁵ wherein R⁵ is alkyl of from one to fifteen carbon atoms, with the proviso that X and Y are not both alkyl, —(CH₂)ₘ-aryl wherein m is zero or an integer of 1, or

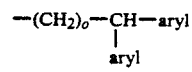

wherein R⁶ and R⁷ are each independently
hydrogen,
alkyl of from one to fifteen carbon atoms,
—(CH₂)ₒ-aryl wherein O is an integer of 1 or 2, $$-(CH_2)_o-\underset{\underset{aryl}{|}}{CH}-aryl$$

wherein O is zero or an integer of 1 or
X and Y are taken together with the phosphorus atom to which they are attached to form a ring denoted by

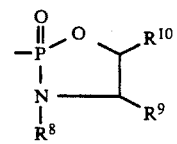

wherein R⁸ is alkyl of from one to six carbon atoms or
—CH₂-aryl and R⁹ and R¹⁰ are each independently
hydrogen,
alkyl of from one to fifteen carbon atoms or
aryl; provided both X and Y are not —OR⁵
wherein R⁵ is alkyl of from one to six carbon atoms or phenyl.

4. A compound according to claim 3 selected from the group consisting of:
(±)-[2-[[2,6-Bis(1-methylethyl)phenyl]amino]-2-oxoethyl]phenylphosphinic acid, ethyl ester;
N-[2,6-Bis(1-methylethyl)phenyl]-2-(diphenylphosphinyl)acetamide;
(±)-[2-Oxo-2-[2,4,6-trimethoxyphenyl)amino]ethyl]-phenylphosphinic acid, ethyl ester;
(±)-[2-[(2,4-Difluorophenyl)amino]-2-oxoethyl]phenylphosphinic acid, ethyl ester;
(±)-[2-[[2,6-Bis(1-methylethyl)phenyl]amino]-2-oxoethyl]phosphonic acid, ethyl nonyl ester;
(±)-[2-[[2,6-Bis(1-methylethyl)phenyl]amino]-2-oxoethyl]-N-(diphenylmethyl)phosphonamidic acid, ethyl ester;
(±)-[2-[[2,6-Bis(1-methylethyl)phenyl]amino-2-oxoethyl]-N,N-bis(phenylmethyl)phosphonamidic acid, ethyl ester;
(±)-[2-[[2,6-Bis(1-methylethyl)phenyl]amino]-2-oxoethyl]phenylphosphinic acid, 1-methyltridecyl ester;
(±)-[2-[[2,6-Bis(1-methylethyl)phenyl]amino]-2-oxoethyl]phenylphosphinic acid, 1-methylheptyl ester;
(±)-2-[[2,6-Bis(1-methylethyl)phenyl]amino]-2-oxoethyl]phenylphosphinic acid, dodecyl ester;
(±)-[2-[[2,6-Bis(1-methylethyl)phenyl]amino]-2-oxoethyl]-N-(2,2-diphenylethyl)phosphonamidic acid, ethyl ester;

[2-[[2,6-Bis(1-methylethyl)phenyl]amino]-2-oxoethyl]-phosphonic acid, bis(phenylmethyl) ester;

(±)-P-[2-[[2,6-Bis(1-methylethyl)phenyl]amino]-2-oxo-ethyl]-N,N-dioctyl phosphonamidic acid, ethyl ester; and (±)-P-[2-[[2,6-Bis(1-methylethyl)phenyl]amino]-2-oxo-ethyl]-N-methyl-N-(2-phenylethyl)phosphonamidic acid, ethyl ester.

5. A method of treating hypercholesterolemia or atherosclerosis comprising administering to a mammal in need of such treatment an acyl-coenzyme A:cholesterol acyltransferase-inhibitory effective amount of a compound as defined in claim 1 in unit dosage form.

6. A pharmaceutical composition for treating hypercholesterolemia or atherosclerosis comprising an acyl-coenzyme A:cholesterol acyltransferase-inhibitory effective amount of a compound as defined in claim 1 in combination with a pharmaceutically acceptable carrier.

* * * * *